United States Patent
Aranyi et al.

(10) Patent No.: US 9,480,492 B2
(45) Date of Patent: Nov. 1, 2016

(54) APPARATUS FOR ENDOSCOPIC PROCEDURES

(71) Applicant: Covidien LP, Mansfield, MA (US)

(72) Inventors: Ernest Aranyi, Easton, CT (US); Dwight G. Bronson, Cheshire, CT (US); David C. Racenet, Killingworth, CT (US)

(73) Assignee: Covidien LP, Mansfield, MA (US)

( * ) Notice: Subject to any disclaimer, the term of this patent is extended or adjusted under 35 U.S.C. 154(b) by 633 days.

(21) Appl. No.: 13/921,890

(22) Filed: Jun. 19, 2013

(65) Prior Publication Data

US 2013/0282052 A1 Oct. 24, 2013

Related U.S. Application Data

(63) Continuation-in-part of application No. 13/891,288, filed on May 10, 2013, which is a continuation-in-part of application No. 13/444,228, filed on Apr. 11, 2012, now Pat. No. 8,672,206, which is a
(Continued)

(51) Int. Cl.
| | |
|---|---|
| *A61B 17/068* | (2006.01) |
| *A61B 17/28* | (2006.01) |
| *A61B 17/072* | (2006.01) |
| *A61B 17/00* | (2006.01) |

(Continued)

(52) U.S. Cl.
CPC ..... *A61B 17/2816* (2013.01); *A61B 17/07207* (2013.01); *A61B 2017/0046* (2013.01); *A61B 2017/00398* (2013.01); *A61B 2017/00477* (2013.01); *A61B 2017/00685* (2013.01); *A61B 2017/07278* (2013.01); *A61B 2017/07285* (2013.01); *A61B 2017/2908* (2013.01); *A61B 2017/2923* (2013.01); *A61B 2017/2927* (2013.01); *A61B 2017/320052* (2013.01)

(58) Field of Classification Search
CPC ............... A61B 17/07207; A61B 2017/2927; A61B 2019/4857; A61B 2017/2933; A61B 2017/2937; A61B 17/320092; A61B 2017/2908; A61B 2017/2929; A61B 17/068; A61B 17/2816
USPC ............................ 227/175.1, 176.1, 180.1
See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |

(Continued)

FOREIGN PATENT DOCUMENTS

| | | |
|---|---|---|
| AU | 2008229795 A1 | 4/2009 |
| CA | 2451558 A1 | 1/2003 |

(Continued)

OTHER PUBLICATIONS

Extended European Search Report from Application No. EP 13171742.3 dated Jan. 3, 2014.
International Search Report corresponding to PCT/US2005/027266, completed May 30, 2008 and mailed Jun. 18, 2008; (2 pp.).
Extended European Search Report corresponding to EP 08 25 3184.9, completed Feb. 12, 2009 and mailed Feb. 27, 2009; (3 pp.).
Extended European Search Report corresponding to EP 10 25 0228.3, completed May 20, 2010 and mailed Jun. 1, 2010; (6 pp.).
Extended European Search Report corresponding to EP 10 25 2037.6, completed Mar. 1, 2011 and mailed Mar. 9, 2011; (3 pp.).

(Continued)

*Primary Examiner* — Michelle Lopez

(57) ABSTRACT

A surgical device has a jaw assembly with a first jaw and a second jaw, a pivoting linkage, and a camming assembly configured to pivot the jaw assembly. A cam slot having a first portion, a second portion, and a third portion may have a Y shaped configuration. A flexible shaft allows further pivoting of the jaw assembly.

6 Claims, 20 Drawing Sheets

Related U.S. Application Data continuation-in-part of application No. 13/280,898, filed on Oct. 25, 2011, now Pat. No. 8,899,462, which is a continuation-in-part of application No. 13/280,859, filed on Oct. 25, 2011, now Pat. No. 8,657,177.

(60) Provisional application No. 61/779,873, filed on Mar. 13, 2013, provisional application No. 61/672,891, filed on Jul. 18, 2012, provisional application No. 61/659,116, filed on Jun. 13, 2012.

(51) Int. Cl.
*A61B 17/29* (2006.01)
*A61B 17/32* (2006.01)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |

(56) References Cited

U.S. PATENT DOCUMENTS

| | | |
|---|---|---|
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2005/0131442 A1 | 6/2005 | Yachia et al. |
| 2005/0222665 A1 | 10/2005 | Aranyi |
| 2006/0142656 A1 | 6/2006 | Malackowski et al. |
| 2006/0142740 A1 | 6/2006 | Sherman et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton, IV et al. |
| 2007/0102472 A1 | 5/2007 | Shelton, IV |
| 2007/0152014 A1 | 7/2007 | Gillum et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0175961 A1 | 8/2007 | Shelton et al. |
| 2008/0029570 A1 | 2/2008 | Shelton, IV et al. |
| 2008/0029573 A1 | 2/2008 | Shelton, IV et al. |
| 2008/0029574 A1 | 2/2008 | Shelton, IV et al. |
| 2008/0029575 A1 | 2/2008 | Shelton, IV et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0119871 A1 | 5/2008 | Brock et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |

(56) References Cited

U.S. PATENT DOCUMENTS

| | | |
|---|---|---|
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0320252 A1* | 12/2010 | Viola .............. A61B 17/07207 227/176.1 |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 101856251 A | 10/2010 |
| CN | 102247182 A | 11/2011 |
| DE | 102008053842 A1 | 5/2010 |
| EP | 0634144 | 1/1995 |
| EP | 0648476 | 4/1995 |
| EP | 0686374 | 12/1995 |
| EP | 0705571 A1 | 4/1996 |
| EP | 1690502 | 8/2006 |
| EP | 1723913 A1 | 11/2006 |
| EP | 1736112 | 12/2006 |
| EP | 1759652 A2 | 3/2007 |
| EP | 1769754 | 4/2007 |
| EP | 1772105 A1 | 4/2007 |
| EP | 1813199 A1 | 8/2007 |
| EP | 1813203 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 | 7/2008 |
| EP | 1943976 | 7/2008 |
| EP | 1952769 A2 | 8/2008 |
| EP | 2005898 A2 | 12/2008 |
| EP | 2027819 | 2/2009 |
| EP | 2044890 A1 | 4/2009 |
| EP | 2055243 | 5/2009 |
| EP | 2090247 A1 | 8/2009 |
| EP | 2098170 | 9/2009 |
| EP | 2100561 | 9/2009 |
| EP | 2100562 A2 | 9/2009 |
| EP | 2333509 | 2/2010 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2377472 A1 | 10/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |

(56) References Cited

FOREIGN PATENT DOCUMENTS

| | | |
|---|---|---|
| EP | 2676615 A2 | 12/2013 |
| EP | 2815705 A1 | 12/2014 |
| ES | 2333509 A1 | 2/2010 |
| FR | 2861574 A1 | 5/2005 |
| JP | 08-038488 | 2/1996 |
| JP | 2005-125075 A | 5/2005 |
| KR | 20120022521 A | 3/2012 |
| WO | 99/15086 A1 | 4/1999 |
| WO | WO 00/72760 | 12/2000 |
| WO | WO 00/72765 | 12/2000 |
| WO | 03/000138 A2 | 1/2003 |
| WO | 03/030743 A2 | 4/2003 |
| WO | WO 03/026511 | 4/2003 |
| WO | 03065916 A1 | 8/2003 |
| WO | WO 03/077769 | 9/2003 |
| WO | 03090630 A2 | 11/2003 |
| WO | WO 2004/107989 | 12/2004 |
| WO | WO 2006/042210 | 4/2006 |
| WO | 2007016290 A2 | 2/2007 |
| WO | WO 2007/014355 | 2/2007 |
| WO | WO 2007/026354 | 3/2007 |
| WO | 2007137304 A2 | 11/2007 |
| WO | WO 2008/131362 | 10/2008 |
| WO | WO 2008/133956 | 11/2008 |
| WO | WO 2009/039506 | 3/2009 |
| WO | WO 2009039506 A1 * | 3/2009 ....... A61B 17/07207 |
| WO | WO 2009/132359 | 10/2009 |
| WO | 2009/143092 A1 | 11/2009 |
| WO | 2009149234 A1 | 12/2009 |
| WO | 2011/108840 A2 | 9/2011 |
| WO | 2012040984 A1 | 4/2012 |

OTHER PUBLICATIONS

Extended European Search Report corresponding to EP 10 25 1968.3, completed on Jul. 4, 2011 and mailed Jul. 14, 2011; (12 pp.).
Extended European Search Report corresponding to EP 11 15 2266.0, completed Jul. 15, 2011 and mailed Jul. 28, 2011; (3 pp.).
Extended European Search Report corresponding to EP 11 25 0462.6, completed Jul. 20, 2011 and mailed Jul. 28, 2011; (6 pp.).
Extended European Search Report corresponding to EP 11 25 0771.0, completed Feb. 7, 2012 and mailed Feb. 17, 2012; (3 pp.).
Extended European Search Report corresponding to EP 06 78 8914.7, completed May 3, 2012 and mailed May 11, 2012; (8 pp.).
Partial European Search Report corresponding to EP 12 18 6177.7, completed Jan. 30, 2013 and mailed Feb. 12, 2013; (6 pp.).
Extended European Search Report corresponding to EP 08 25 2703.7, completed Oct. 23, 2008 and mailed Oct. 31, 2008; (7 pp.).
Extended European Search Report corresponding to EP No. 11 17 8021.9, mailed Jun. 4, 2013; (3 pp).
Extended European Search Report corresponding to EP No. 13 16 3033.7, completed Jun. 27, 2013 and mailed Jul. 15, 2013; (8 pp).
Extended European Search Report corresponding to EP No. 12 18 6177.7, completed Aug. 14, 2013 and mailed Aug. 23, 2013; (8 pp).
Partial European Search Report corresponding to EP No. 13 17 1742.3, completed Sep. 17, 2013 and mailed Sep. 25, 2013; (8 pp).
Partial European Search Report corresponding to EP No. 13 17 2400.7, completed Sep. 18, 2013 and mailed Oct. 1, 2013; (7 pp).
Extended European Search Report corresponding to EP No. 13 17 5475.6, completed Sep. 23, 2013 and mailed Oct. 1, 2013; (8 pp).
Extended European Search Report corresponding to EP No. 13 17 5478.0, completed Sep. 24, 2013 and mailed Oct. 2, 2013; (6 pp).
Extended European Search Report corresponding to EP No. 13 17 5479.8, completed Sep. 27, 2013 and mailed Oct. 10, 2013; (7 pp).
Partial Extended European Search Report corresponding to EP 13 17 5477.2, completed Oct. 7, 2013 and mailed Oct. 15, 2013; (7 pp).
Extended European Search Report corresponding to EP No. 08 25 2703.7, completed Oct. 23, 2008 and mailed Oct. 31, 2008; (7 pp).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
The extended European Search Report from Application No. 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report from Application No. EP 13176805.3 dated Mar. 20, 2014.
Extended European Search Report corresponding to EP 13 17 6805.3, completed Oct. 22, 2013 and mailed Nov. 4, 2013; (8 pp).
EP Examination Report for Application No. 13 176 805.3 dated Mar. 27, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, mailed Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action for application No. 201310303808.2 dated Aug. 8, 2016.

* cited by examiner

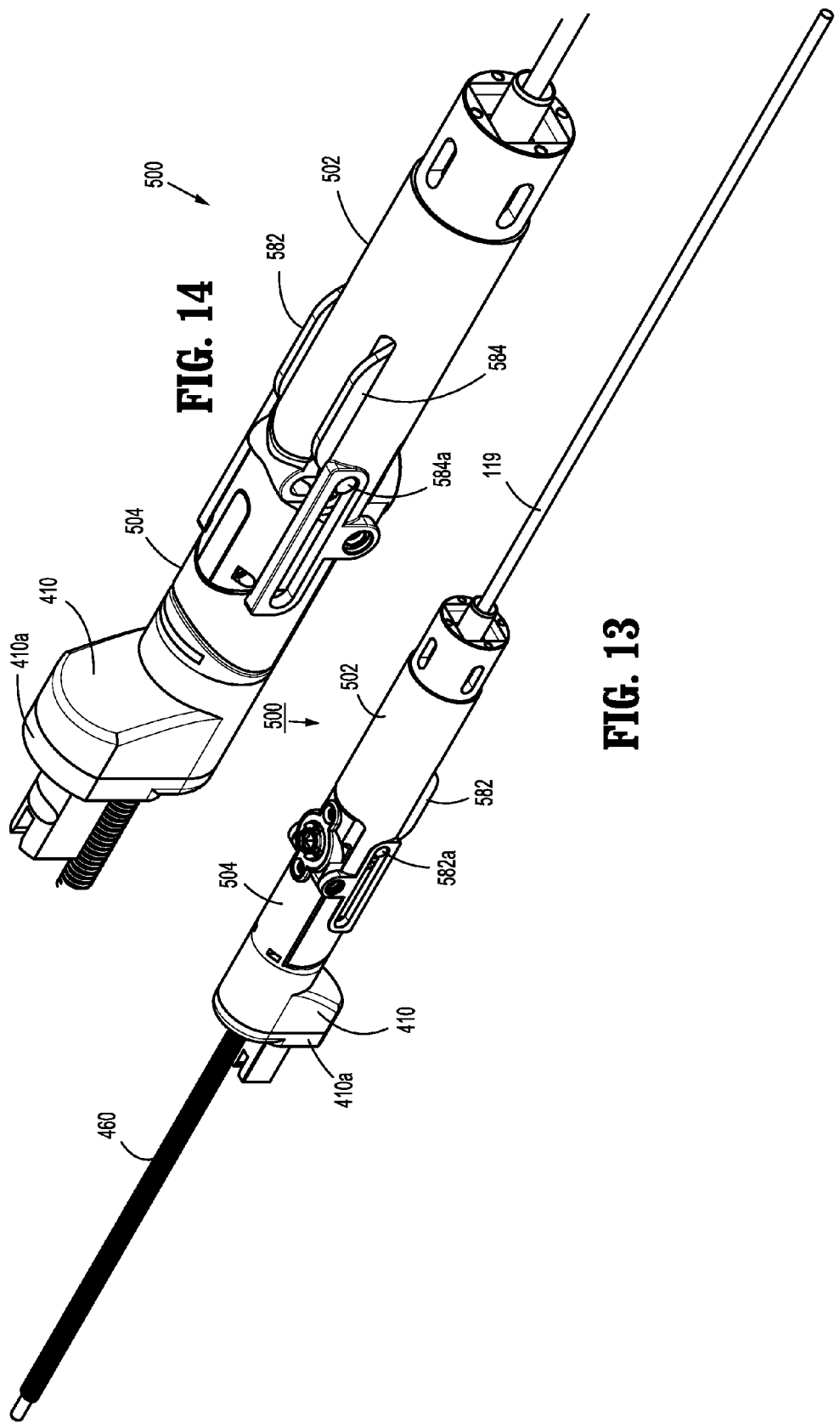

APPARATUS FOR ENDOSCOPIC PROCEDURES

CROSS-REFERENCE TO RELATED APPLICATIONS

This application is a continuation-in-part of U.S. patent application Ser. No. 13/891,288, filed on May 10, 2013, which is a continuation-in-part of U.S. patent application Ser. No. 13/444,228, filed on Apr. 11, 2012, now U.S. Pat. No. 8,672,206, which is a continuation-in-part of U.S. patent application Ser. No. 13/280,898, filed on Oct. 25, 2011, now U.S. Pat. No. 8,899,462, which is a continuation-in-part of U.S. patent application Ser. No. 13/280,859, filed on Oct. 25, 2011, now U.S. Pat. No. 8,657,177, and also claims the benefit of and priority to U.S. Provisional Patent Application No. 61/779,873, filed on Mar. 13, 2013, and U.S. Provisional Patent Application No. 61/672,891, filed on Jul. 18, 2012, and U.S. Provisional Patent Application No. 61/659,116, filed on Jun. 13, 2012, the entire content of each of which is incorporated herein by reference.

BACKGROUND

1. Technical Field

The present disclosure relates to surgical apparatuses, devices and/or systems for performing endoscopic surgical procedures and methods of use thereof. More specifically, the present disclosure relates to electromechanical, hand-held surgical apparatus, devices and/or systems configured for use with removable disposable loading units and/or single use loading units for clamping, cutting and/or stapling tissue.

2. Background of Related Art

Surgical devices for grasping or clamping tissue between opposed jaw structure of a tool assembly and thereafter fastening the clamped tissue are well known in the art. These devices may include a knife for incising the fastened tissue. The fasteners are typically in the form of surgical staples but two part fasteners formed of a material suitable for surgical use are also well known.

Typically, the tool member includes a staple cartridge which houses a plurality of staples arranged in at least two laterally spaced rows and an anvil which includes a plurality of staple forming pockets for receiving and forming staple legs of the staples as the staples are driven from the cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples.

In laparoscopic and/or endoscopic surgical procedures, the surgical procedure is performed through a small incision or through a narrow cannula inserted through a small entrance wound in a patient. Because of reduced patient trauma, shortened patient recovery periods and substantial reduction in overall cost, laparoscopic procedures are preferred over open procedures. In order to address the specific needs of endoscopic and/or laparoscopic surgical procedures, endoscopic surgical stapling devices have been developed which provide a surgeon with easier access to the operative site. Typically, these stapling devices include an articulatable tool member which is supported adjacent to the distal end of the stapling device. The tool member can be selectively manipulated to allow a surgeon to manipulate a tool assembly in a confined space. There is a need for improved articulation and/or pivoting mechanisms that allow the surgeon to manipulate the tool member in a variety of configurations.

SUMMARY

Further details and aspects of exemplary embodiments of the present invention are described in more detail below with reference to the appended Figures.

In an aspect of the present disclosure, a surgical device, comprises a jaw assembly including a first jaw and a second jaw moveable relative to the first jaw. A pivoting linkage coupled to the proximal end of the jaw assembly, the pivoting linkage comprising a distal joint member and a proximal joint member. The jaw assembly and the distal joint member define a first longitudinal axis extending between a proximal end of the jaw assembly and a distal end of the distal joint member, and the proximal joint member defines a second longitudinal axis. The device includes a camming assembly configured to pivot the jaw assembly relative to the proximal joint member about a pivot axis that is perpendicular to the first and second longitudinal axes.

The device can include a handle assembly and an elongated body configured to interconnect the handle assembly and the jaw assembly. The elongated body can comprise a flexible shaft coupled to the proximal end of the proximal joint member and a rigid shaft portion coupled to the proximal end of the flexible shaft, wherein the rigid shaft portion defines a third longitudinal axis and the flexible shaft is configured to articulate the jaw assembly and the pivoting linkage relative to the third longitudinal axis of the rigid shaft.

In certain embodiments, the distal joint member has a cam slot at the proximal end of the distal joint member and the device further comprises a cam pin disposed in the cam slot. The cam slot can have a first portion, a second portion, and a third portion; the first portion, second portion and third portion extending at an angle with respect to one another. In certain embodiments, the cam slot has a Y shaped configuration. The device can comprise a movable clevis having the cam pin.

In certain embodiments, the distal joint member comprises a pair of opposing cam slots and the proximal joint member has a clevis associated therewith, the clevis having a pair of camming pins disposed within the pair of opposing cam slots such that movement of the clevis pivots the jaw assembly relative to the proximal joint member about the pivot axis.

The device can further comprise a drive screw disposed within the jaw assembly; and a drive shaft disposed within the pivoting linkage, the drive shaft configured to engage the drive screw and to rotate in a first direction to move the second jaw relative to the first jaw.

In certain embodiments, the device further comprises a rotation link disposed within the proximal joint member, the rotation link defining a lumen therethrough in which the drive shaft is disposed.

The pivoting linkage can further comprise a primary gearing assembly. The primary gearing assembly comprises a primary first gear coupled to the jaw assembly configured to rotate the jaw assembly about the first longitudinal axis and a primary second gear coupled to the drive shaft. The pivoting linkage can include a secondary gearing assembly having a secondary first gear coupled to the primary first gear, the secondary first gear configured to rotate the jaw assembly about the first longitudinal axis when the jaw assembly and the distal joint member are in a pivoted configuration, and a secondary second gear coupled to the primary second gear, the secondary second gear configured to move the second jaw relative to the first jaw.

The rotation link can be movable in a distal direction by the clevis and is configured to engage the secondary first gear when the jaw assembly and the distal joint member are in the pivoted configuration. In certain embodiments, the drive shaft is configured to engage the rotation link when in a proximal position and to rotate in the first direction to rotate the jaw assembly about the first longitudinal axis when the jaw assembly and the distal joint member are in the pivoted configuration.

The drive shaft can be configured to engage the secondary second gear in a distal position and to rotate in the first direction to move the second jaw relative to the first jaw.

In a further aspect of the present disclosure, a surgical device comprises a jaw assembly having a first jaw and a second jaw moveable relative to the first jaw, and a drive screw configured to move the second jaw relative to the first jaw. The device has a pivoting linkage coupled to the proximal end of the jaw assembly, the pivoting linkage comprising a distal joint member and a proximal joint member, wherein the jaw assembly and the distal joint member define a first longitudinal axis extending between a proximal end of the jaw assembly and a distal end of the distal joint member, and the proximal joint member defines a second longitudinal axis. The device includes a camming assembly coupled to the distal and proximal joint members, the camming assembly configured to pivot the jaw assembly relative to the proximal joint member about a pivot axis that is perpendicular to the first and second longitudinal axes from an aligned configuration in which the first and second longitudinal axes are substantially parallel to each other into a pivoted configuration in which the first and second longitudinal axes are substantially perpendicular to each other.

The device can include a drive shaft disposed within the pivoting linkage, the drive shaft configured to engage the drive screw and to rotate in a first direction to move the second jaw relative to the first jaw when the jaw assembly is in one of the aligned configuration and the pivoted configuration. In certain embodiments, in the aligned configuration, the drive shaft is configured to engage the drive screw directly.

In certain embodiments, the pivoting linkage further comprises a primary gearing assembly having a primary first gear coupled to the jaw assembly configured to rotate the jaw assembly about the first longitudinal axis. and a primary second gear coupled to the drive screw configured to move the second jaw relative to the first jaw.

The pivoting linkage can have a secondary gearing assembly comprising a secondary first gear coupled to the primary first gear, the secondary first gear configured to rotate the jaw assembly about the first longitudinal axis when the jaw assembly and the distal joint member are in a pivoted configuration, and a secondary second gear coupled to the primary second gear, the secondary second gear configured to move the second jaw relative to the first jaw.

In certain embodiments, in the pivoted configuration, the drive shaft is configured to engage the drive screw through the secondary second gear.

In another aspect of the present disclosure, a surgical device comprises a jaw assembly including a first jaw and a second jaw movable relative to the first jaw, a pivoting linkage coupled to the proximal end of the jaw assembly, the pivoting linkage comprising a distal joint member and a proximal joint member, wherein the jaw assembly and the distal joint member define a first longitudinal axis extending between a proximal end of the jaw assembly and a distal end of the distal joint member, and the proximal joint member defines a second longitudinal axis, the jaw assembly being pivotable relative to the proximal joint member about a pivot axis that is perpendicular to the first and second longitudinal axis. The device includes a flexible shaft proximal of the pivoting linkage, the flexible portion having a plurality of openings accommodating a plurality of cables for effectuating the flexing of the flexible portion.

The flexible shaft may include a plurality of segments, each segment having a ball joint at a distal end thereof, and a proximal end defining a socket. The distal joint member may have a cam slot at the proximal end of the distal joint member and further comprising a cam pin disposed in the cam slot.

The cam slot may have a first portion, a second portion, and a third portion, the first portion, second portion and third portion extending at an angle with respect to one another. The cam slot may have a Y shaped configuration. In certain embodiments, the device includes a movable clevis having the cam pin.

In certain embodiments, the distal joint member comprises a pair of opposing cam slots and the proximal joint member has a clevis associated therewith, the clevis having a pair of camming pins disposed within the pair of opposing cam slots such that movement of the clevis pivots the jaw assembly relative to the proximal joint member about the pivot axis.

BRIEF DESCRIPTION OF THE DRAWINGS

Embodiments of the present disclosure are described herein with reference to the accompanying drawings, wherein:

FIG. 13 is a perspective, bottom view of a pivoting linkage of the end effector of FIG. 1, according to the present disclosure;

FIG. 14 is a perspective, top view of the pivoting linkage of FIG. 13, according to the present disclosure;

DETAILED DESCRIPTION OF EMBODIMENTS

Figure 1:
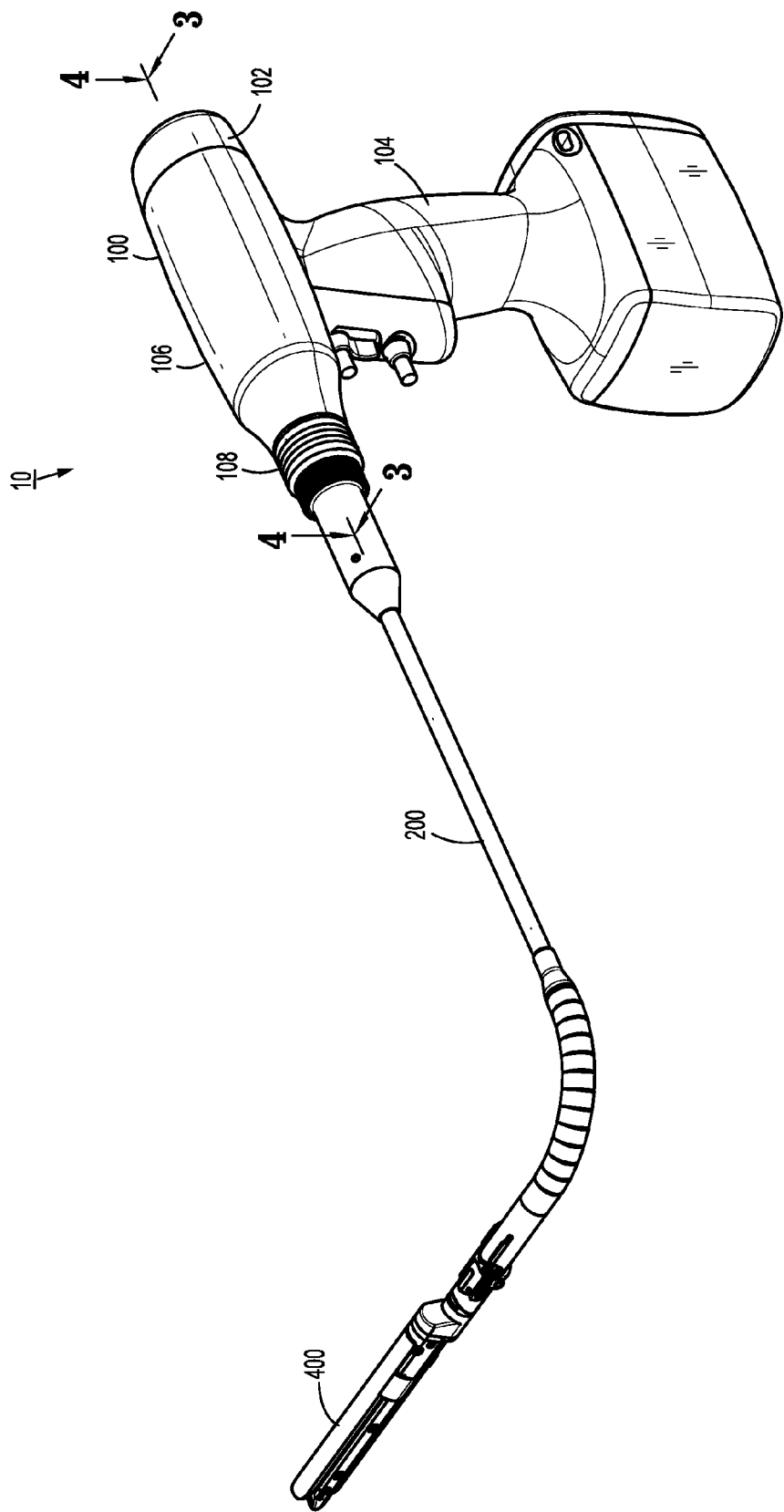
FIG. 1 is a perspective view of an electromechanical surgical system according to the present disclosure.
Figure 2:
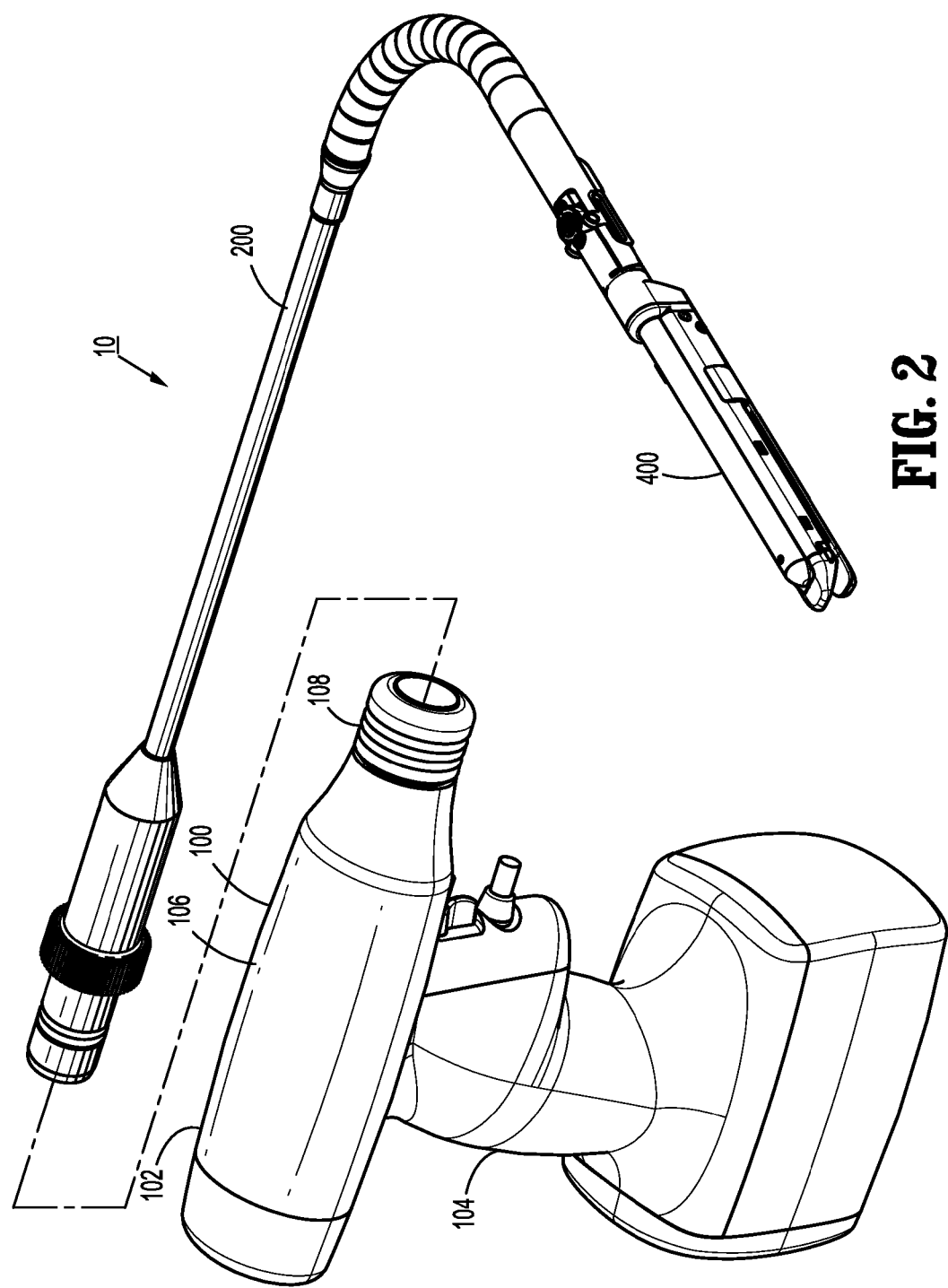
FIG. 2 is a disassembled, perspective view of a surgical instrument, an elongated member, and an end effector of the electrosurgical surgical system of FIG. 1, according to the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user. The terms "left" and "right" refer to that portion of the electromechanical surgical system, apparatus and/or device, or component thereof, that are on the left (e.g., port) and right (e.g., starboard) sides, respectively, from the perspective of the user facing the distal end of the electromechanical surgical system, apparatus and/or device from the proximal end while the surgical system, apparatus and/or device is oriented in non-rotational configuration.

Referring initially to FIGS. 1-5, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical instrument 100 that is configured for selective attachment thereto of a plurality of different end effectors 400, via a shaft assembly 200. The end effector 400 and the shaft assembly 200 are configured for actuation and manipulation by the electromechanical, hand-held, powered surgical instrument 100. In particular, the surgical instrument 100, the shaft assembly 200, and the end effector 400 are separable from each other such that the surgical instrument 100 is configured for selective connection with shaft assembly 200, and, in turn, shaft assembly 200 is configured for selective connection with any one of a plurality of different end effectors 400.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, the entire content of each of which is incorporated herein by reference, for a detailed description of the construction and operation of exemplary electromechanical, hand-held, powered surgical instrument 100.

Figure 3:
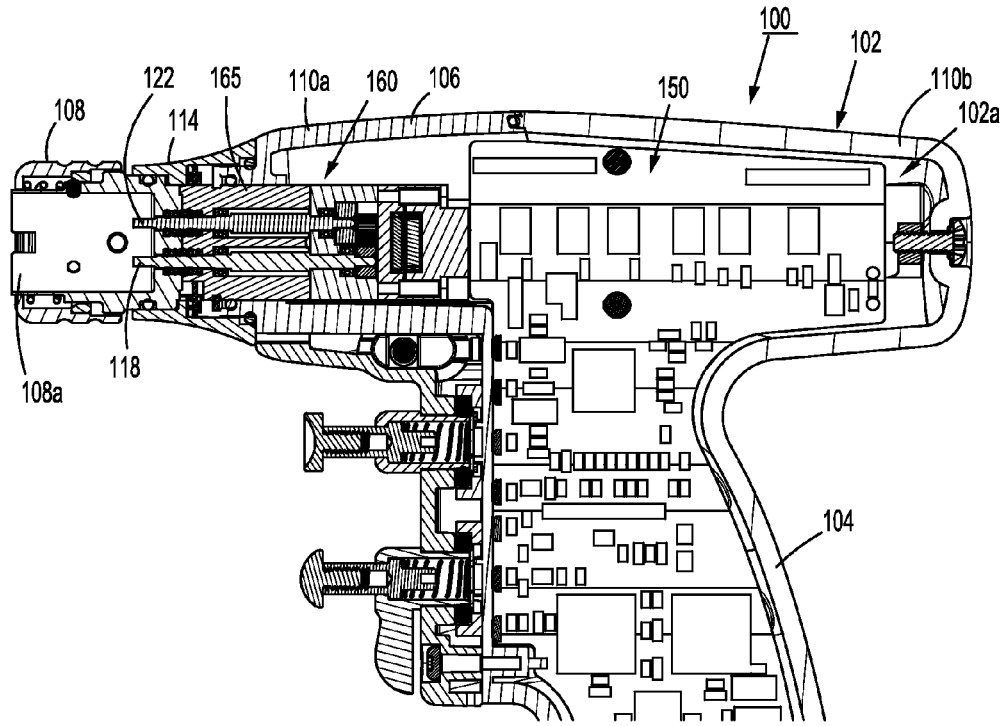
FIG. 3 is a side, cross-sectional view of the surgical instrument of FIG. 1, as taken through 3-3 of FIG. 1, according to the present disclosure.
Figure 4:
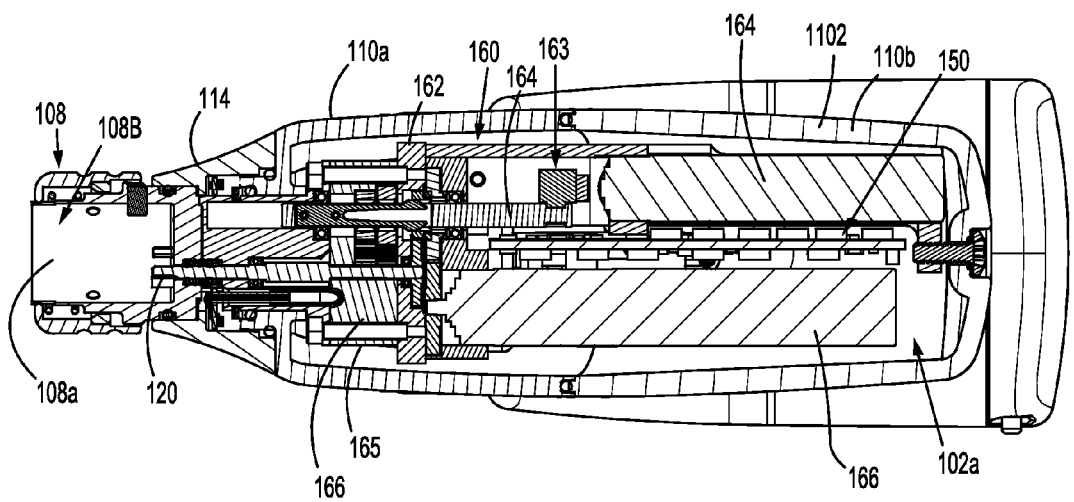
FIG. 4 is a top, cross-sectional view of the surgical instrument of FIG. 1, as taken through 4-4 of FIG. 1, according to the present disclosure.

Generally, as illustrated in FIGS. 1-4, surgical instrument 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners (FIGS. 3 and 4). When joined, distal and proximal half-sections 110a, 110b define the handle housing 102 having a cavity 102a therein in which a control assembly 150 and a drive mechanism 160 are disposed. The instrument 100 also includes a power source (not shown), which is coupled to the control assembly 150 and the drive mechanism 160. Control assembly 150 may include one or more logic controllers and/or user interfaces (e.g., switches, buttons, triggers, touch screens, etc.) and is configured to control the various operations of the instrument 100, in particular, the drive mechanism 160, as discussed in further detail below.

Lower housing portion 104 of the instrument 100 defines an aperture (not shown) formed in an upper surface thereof and which is located beneath or within intermediate housing portion 106. The aperture of lower housing portion 104 provides a passage through which wires and other various electrical leads interconnect electrical components (e.g., power source and any corresponding power control circuitry) situated in lower housing portion 104 with electrical components (e.g., control assembly 150, drive mechanism 160, etc.) situated in intermediate housing portion 106 and/or upper housing portion 108.

With reference to FIGS. 3 and 4, distal half-section 110a of upper housing portion 108 defines a nose or connecting portion 108a. A nose cone 114 is supported on nose portion 108a of upper housing portion 108. Upper housing portion 108 of handle housing 102 provides a housing in which drive mechanism 160 is disposed. The drive mechanism 160 is configured to drive shafts and/or gear components in order to perform the various operations of instrument 100. In particular, drive mechanism 160 is configured to drive shafts and/or gear components in order to selectively rotate the end effector 400 about a longitudinal axis A-A defined by the a rigid portion 204 of the shaft assembly 200 (FIG. 6) relative to the handle housing 102, to move jaw members of the end effector 400 relative to each other, and/or to fire the fasteners, to cut the tissue grasped within the end effector 400.

Figure 5:
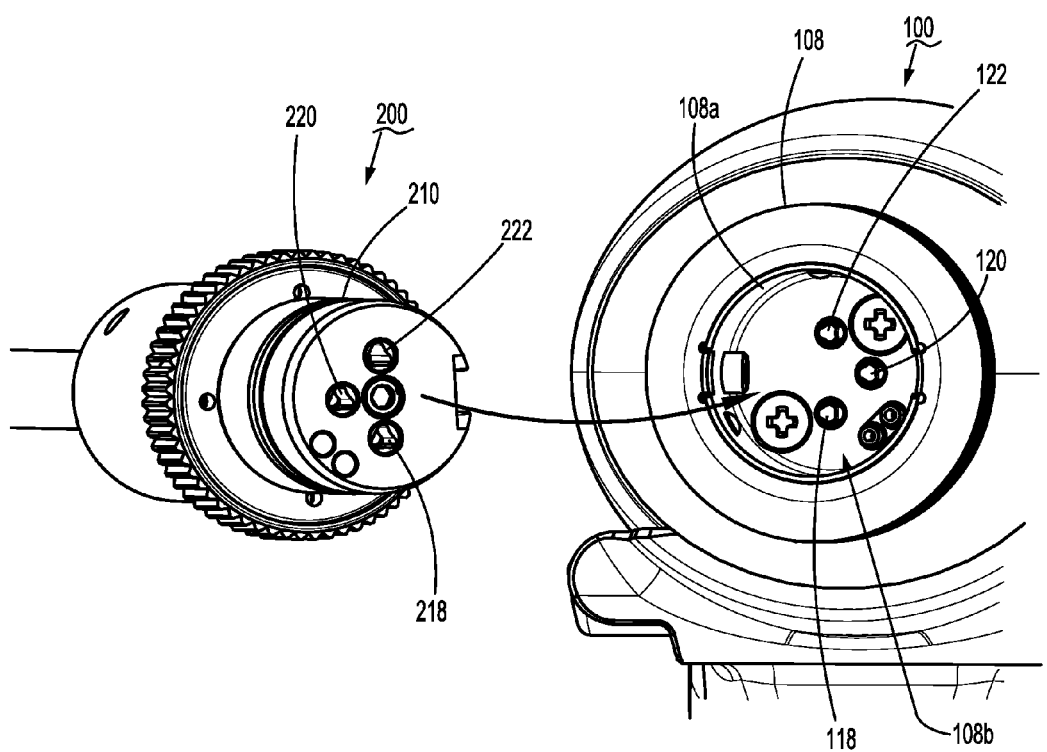
FIG. 5 is a front, perspective view of the surgical instrument of FIG. 1 with the elongated member of FIG. 2 separated therefrom, according to the present disclosure.

As seen in FIGS. 3 and 4, drive mechanism 160 includes a selector gearbox assembly 162 that is located immediately proximal relative to a shaft assembly 200. Proximal to the selector gearbox assembly 162 is a function selection module 163 having a first motor 164 that functions to selectively move gear elements within the selector gearbox assembly 162 into engagement with an input drive component 165 having a second motor 166. With particular reference to FIG. 5, the distal half-section 110a of upper housing portion 108 defines a connecting portion 108a configured to accept a corresponding drive coupling assembly 210 of the shaft assembly 200.

With continued reference to FIG. 5, the connecting portion 108a of instrument 100 includes a cylindrical recess 108b that receives the drive coupling assembly 210 of shaft assembly 200. Connecting portion 108a houses three rotatable drive connectors 118, 120, 122. When shaft assembly 200 is mated to instrument 100, each of rotatable drive connectors, namely, first drive connector 118, second drive connector 120, and third drive connector 122 of instrument 100, mechanically engage a corresponding rotatable connector sleeve, namely, first connector sleeve 218, second connector sleeve 220, and third connector sleeve 222 of shaft assembly 200.

The mating of drive connectors 118, 120, 222 of instrument 100 with connector sleeves 218, 220, 222 of shaft assembly 200 allows rotational forces to be independently transmitted via each of the three respective connector interfaces. The drive connectors 118, 120, 122 of instrument 100 are configured to be independently rotated by drive mechanism 160. In this regard, the function selection module 163 of drive mechanism 160 selects which drive connector or connectors 118, 120, 122 of instrument 100 is to be driven by the input drive component 165 of drive mechanism 160.

With continued reference to FIGS. 3 and 4, drive mechanism 160 includes a selector gearbox assembly 162 and a function selection module 163, located proximal to the selector gearbox assembly 162 that functions to selectively move gear elements within the selector gearbox assembly 162 into engagement with second motor 166. Thus, drive mechanism 160 selectively drives one or more of drive connectors 118, 120, 122 of instrument 100 at a given time.

Since each of drive connectors 118, 120, 122 of instrument 100 has a keyed and/or substantially non-rotatable interface with respective connector sleeves 218, 220, 222 of shaft assembly 200, when shaft assembly 200 is coupled to instrument 100, rotational force(s) are selectively transferred from drive mechanism 160 of instrument 100 to shaft assembly 200.

The selective rotation of drive connector(s) 118, 120 and/or 122 of instrument 100 allows instrument 100 to selectively actuate different functions of the end effector 400. In embodiments, any number of the drive connectors 118, 120, and/or 122 may be used to operate the end effector 400. As will be discussed in greater detail below, selective and independent rotation of first drive connector 118 of instrument 100 corresponds to the selective and independent opening and closing of the jaw members of the end effector 400, and driving of the actuation sled 440 (FIG. 8) of end effector 400. The selective and independent rotation of the third drive connectors 120, 122 of instrument 100 corresponds to the selective and independent pivoting of the end effector 400 relative to the shaft assembly 200.

Figure 6:
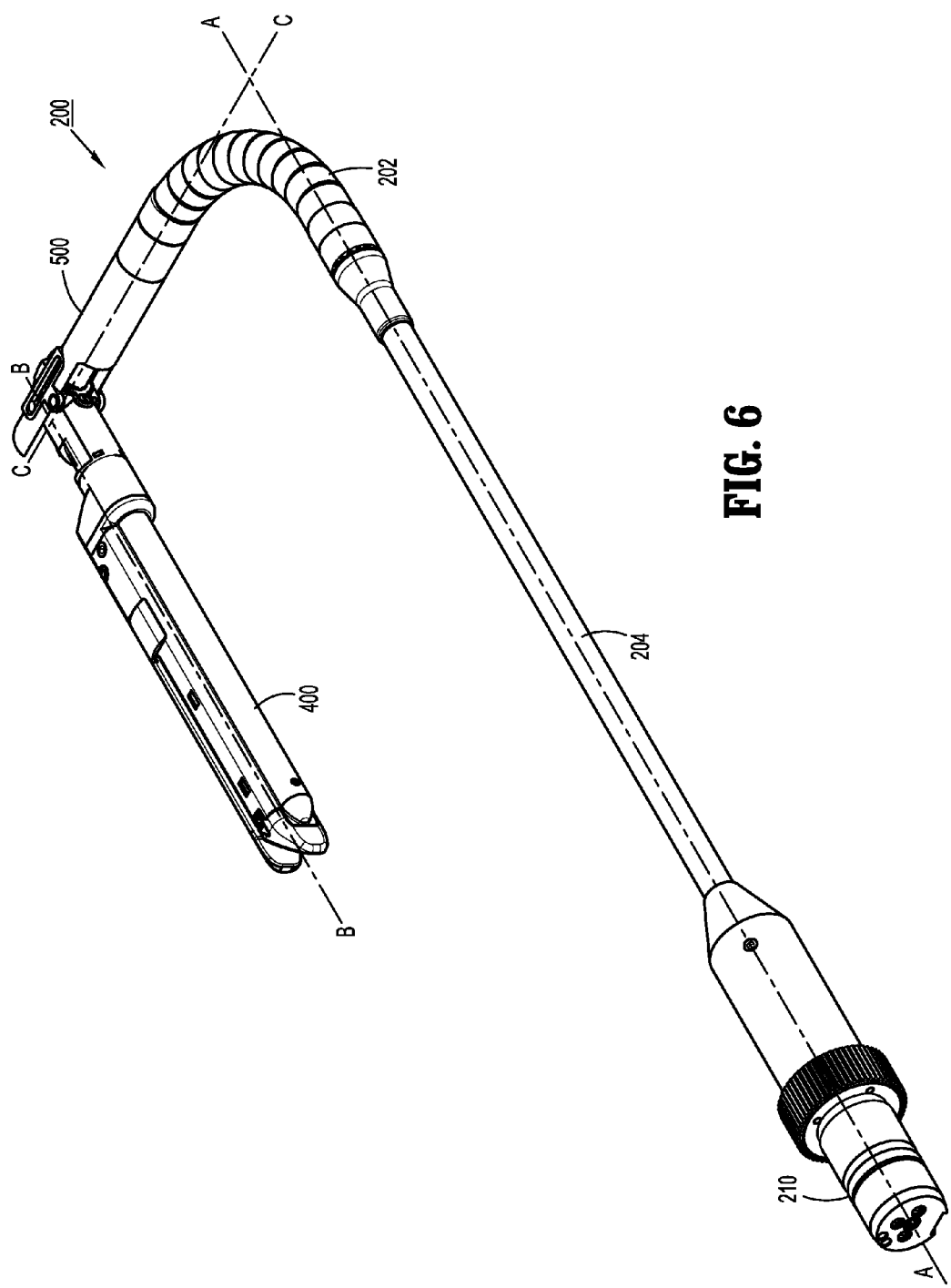
FIG. 6 is a front, perspective view of the elongated member and the end effector of FIG. 1 in articulated and pivoted configurations according to the present disclosure.
Figure 7:
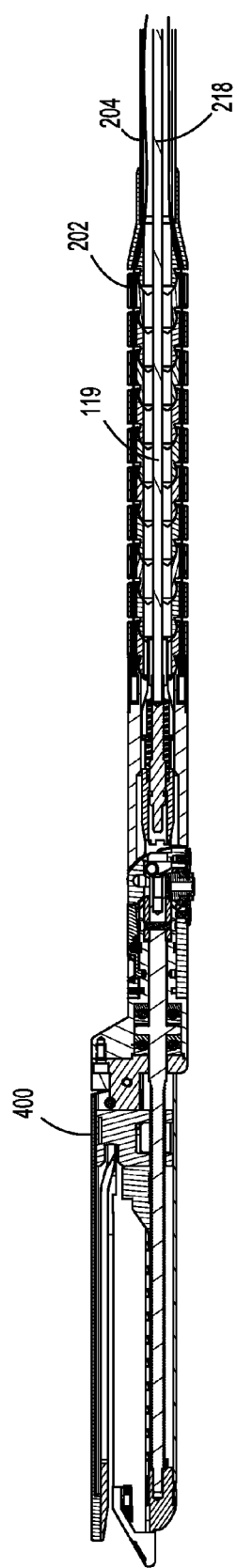
FIG. 7 is a side, cross-sectional view of the end effector of FIG. 1, according to the present disclosure.
Figure 8:
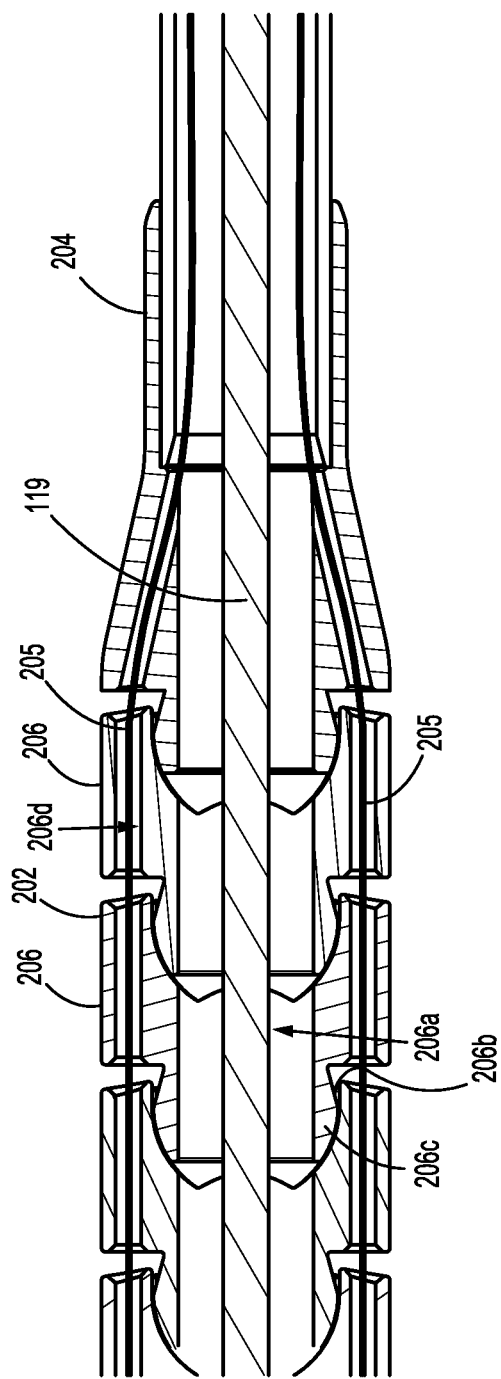
FIG. 8 is an enlarged, side, cross-sectional view of the end effector of FIG. 1, according to the present disclosure.

FIG. 6 shows the shaft assembly 200 and the end effector 400. The shaft assembly 200 includes rigid portion 204 at its proximal end interconnecting drive coupling assembly 210 and a flexible portion or flexible shaft 202. The shaft assembly 200 also includes a pivoting linkage 500 interconnecting the flexible portion 202 and the end effector 400. As shown in FIGS. 7 and 8, the rigid portion 204 houses the first connector sleeve 218, which is coupled to a flexible drive shaft 119 extending through flexible shaft 202. The shaft 119 may be formed from any suitable flexible and torsionally stiff material that may be articulated along with the flexible shaft 202 to allow for the articulation of the end effector 400 relative to the rigid portion 204 between a non-articulated position in which a longitudinal axis B-B defined by the end effector 400 is substantially aligned with axis A-A defined by the rigid portion 204; and an articulated position in which the longitudinal axis of end effector 400 is disposed at a substantially non-zero angle relative to the axis A-A of the rigid portion 204. Shaft 119 may be fabricated from stainless steel or the like.

As seen in FIG. 8, the flexible shaft 202 includes a plurality of interlocking segments 206 each defining an opening 206a therethrough. The shaft 119 is disposed within the openings 206a as shown in FIG. 8. Each of the interlocking segments 206 includes a socket 206b at its proximal end and a ball joint 206c at its distal end. The ball joint 206c of one segment 206 is configured and dimensioned to interface with the socket 206b of the distal neighboring segment 206 allowing the entire flexible shaft 202 to flex and thereby articulate in any desired direction through 360° around a longitudinal axis of rigid portion 204. In particular, articulation of the flexible shaft 202 allows for articulation of the end effector 400 and pivoting linkage 500 with respect to the axis A-A.

Figure 9:
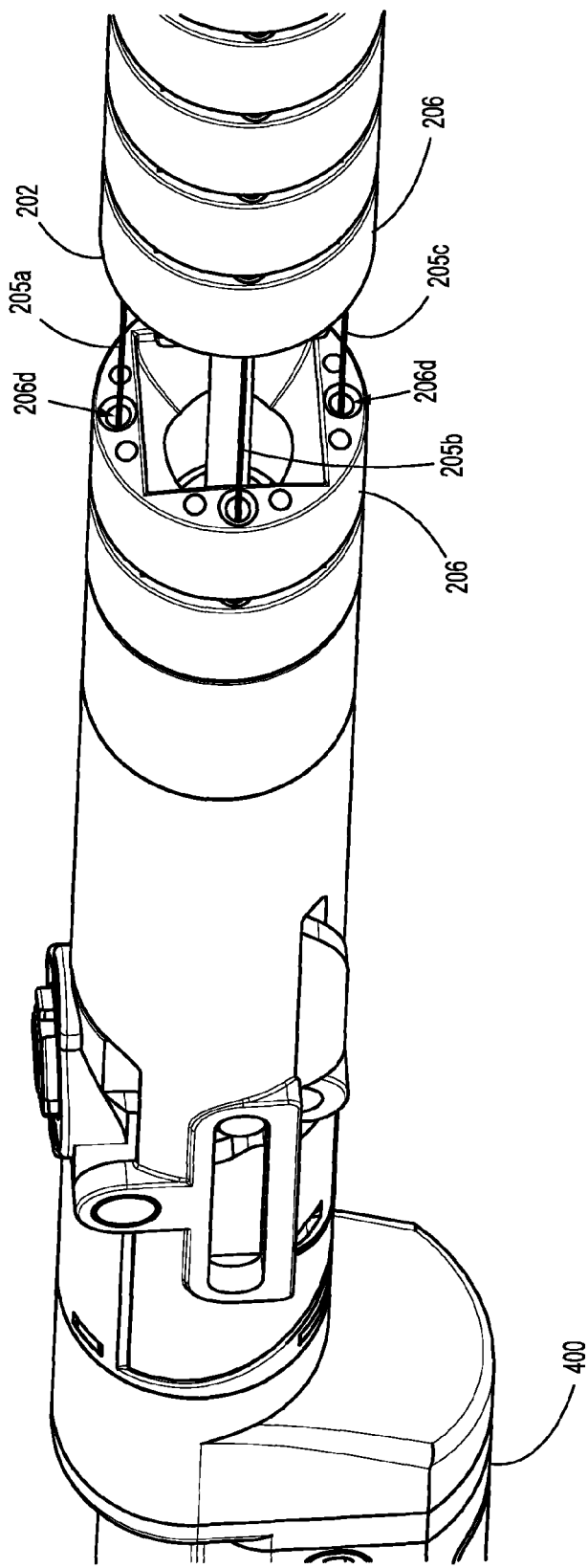
FIG. 9 is an enlarged, perspective, rear view of the end effector of FIG. 1, according to the present disclosure.
Figure 10:
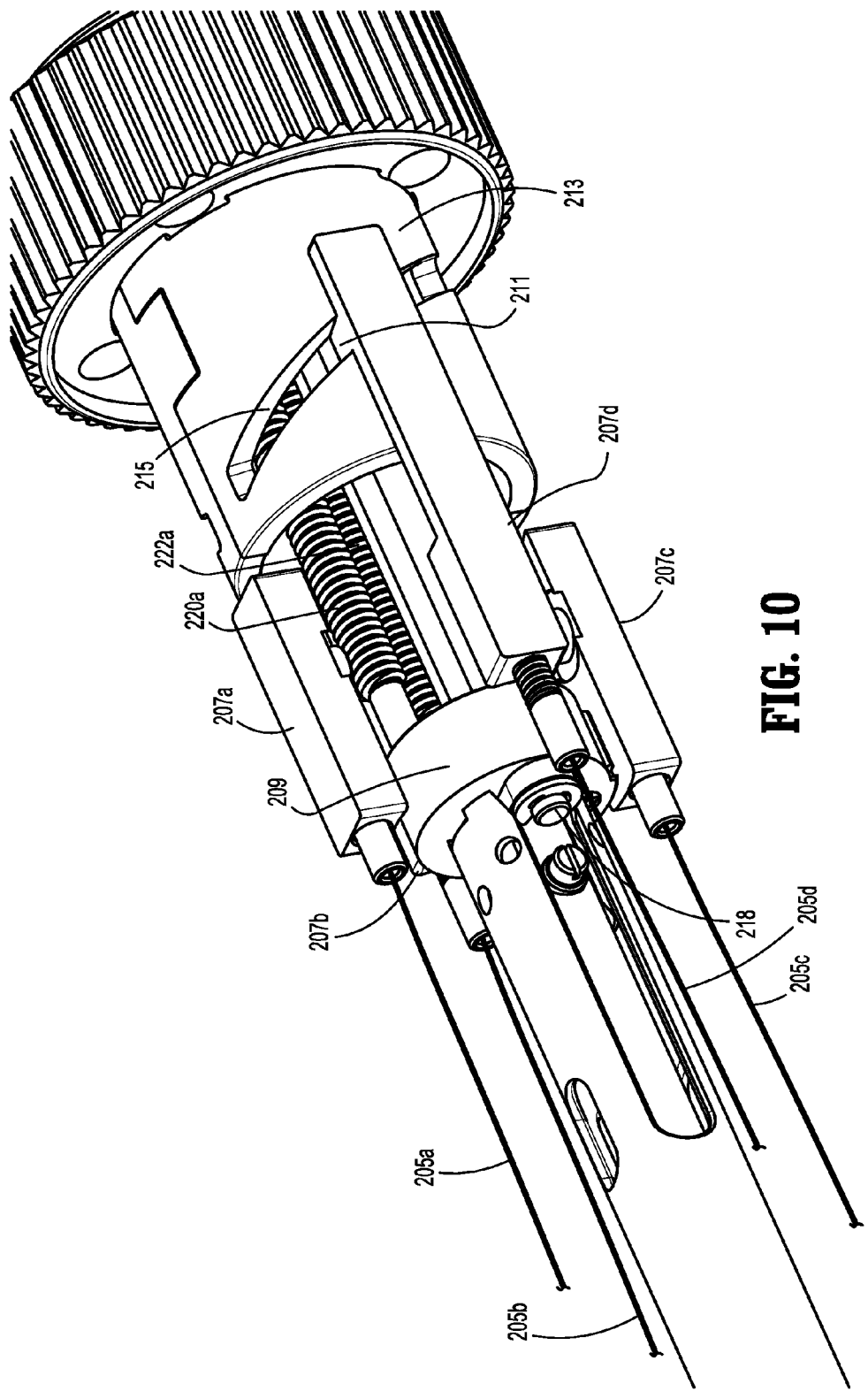
FIG. 10 is a side, partially-exploded view of a drive coupling assembly according to the present disclosure.

With reference to FIGS. 9 and 10, articulation of the flexible portion 202 may be accomplished by tensioning cables 205a, 205b, 205c, 205d. In embodiments, four equally radially-spaced apart cables may be used, which are coupled to the end effector 400 and which pass through the flexible shaft 202. In particular, as shown in FIGS. 9 and 10, each of the cables 205a, 205b, 205c, 205d may be disposed within a respective opening 206d of the segments 206. Thus, tension applied to one or more of cables would adjust a direction of articulation of the flexible shaft 202. A cable articulation instrument is disclosed in a commonly-owned U.S. Provisional Patent Application No. 61/510,091, filed on Jul. 21, 2011, entitled "Articulating Links With Middle Link Control System", the entire contents of which are incorporated by reference herein.

With reference to FIG. 10, the drive coupling assembly 210 is shown having each of the cables 205a, 205b, 205c, 205d coupled to anchor bars 207a, 207b, 207c, 207d, respectively. The cables 205a, 205b, 205c, 205d may be secured to the bars 207a, 207b, 207c, 207d by any suitable means including, but not limited to, adhesive, knots, etc. The bars 207a, 207b, 207c, 207d are coupled to an attachment ring 209 in an equally radially-spaced apart configuration to maintain radial alignment of the cables 205a, 205b, 205c, 205d. The bars 207a, 207b, 207c are fixedly coupled to the ring 209 whereas the bar 207d is slidingly coupled thereto such that the bar 207d can move longitudinally relative to the ring 209. The bar 207d includes a detent 211 that is disposed within a slot 215 of a cylinder 213. The slot 215 is defined diagonally through the cylinder 213 with respect the axis A-A.

The ring 209 may be threadably coupled to one or more threaded drive shafts 220a and 222a. As the drive shafts 220a and 222a are rotated, the ring 209 travels in a longitudinal direction along the longitudinal axis defined by the drive shafts 220a and 222a. Rotation of the drive shafts 220a and 222a is imparted through the connection sleeves 220 and 222 as described above. As the ring 209 travels distally in a longitudinal direction, the bars 207a, 207b, 207c are moved distally as well, thereby tensioning cables 205a, 205b, 205c.

The cable 205d is tensioned independently of the cables 205a, 205b, 205c, allowing the end effector 400 to be articulated through the flexible shaft 202 with respect to the longitudinal axis A-A. Specifically, as the tension that is applied on the cable 205d is higher than that applied on the cables 205a, 205b, 205c, the flexible shaft 202 is bent in the direction of the cable 205d. Differential tension on the cable 205d is applied via the bar 207d which is actuated by the cylinder 213. As cylinder 213 is rotated about the longitudinal axis A-A, longitudinal movement is imparted to the bar 207d due to the engagement of the detent 211 of bar 207d and the slot 215 of cylinder 213. In particular, as the cylinder 213 is rotated in a clockwise direction about the axis A-A the bar 207d is moved proximally thereby increasing tension on the cable 207d. Conversely, as the cylinder 213 is rotated in a counterclockwise direction, the bar 207d is moved distally thereby loosening tension on the cable 207d.

Figure 11:
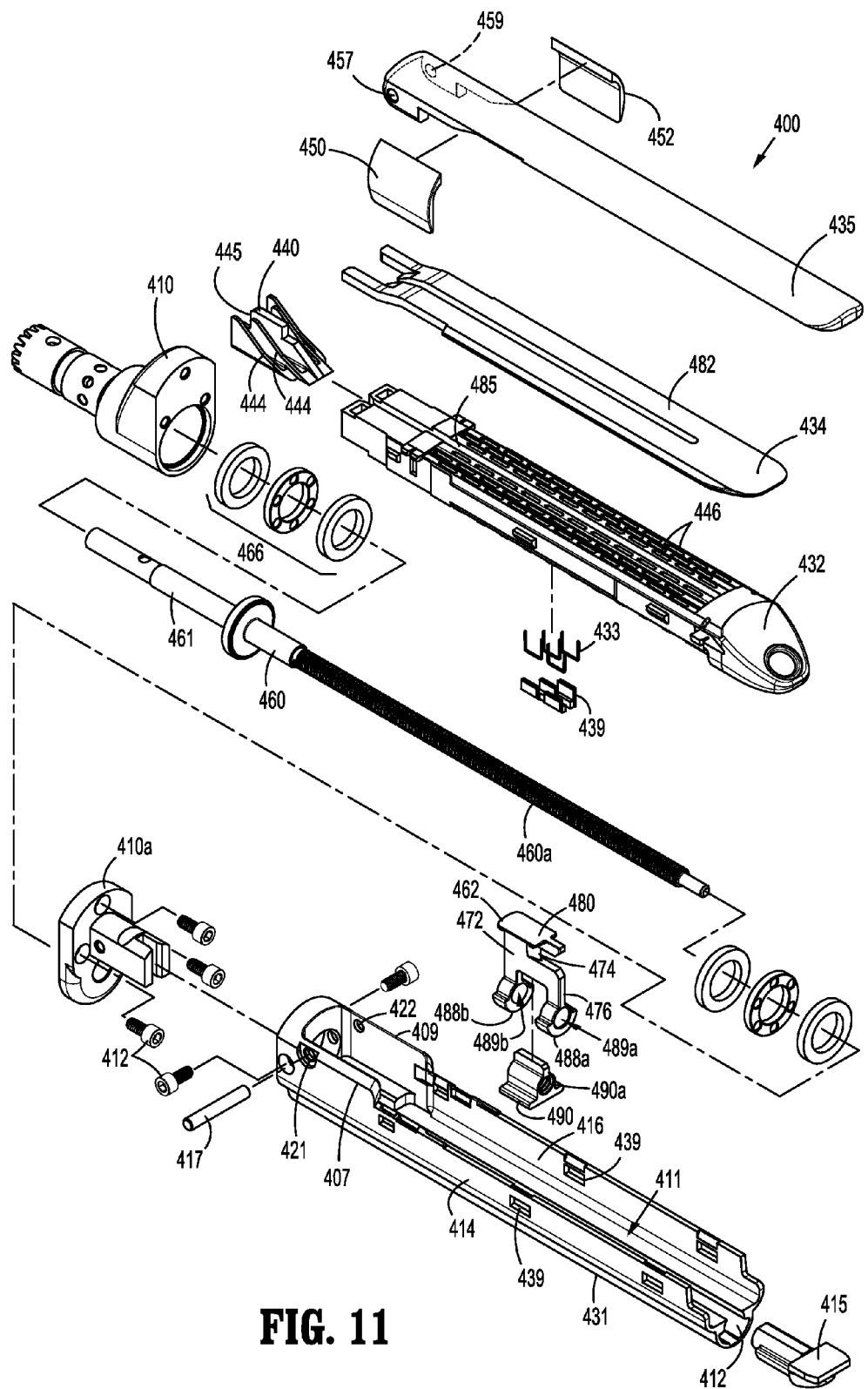
FIG. 11 is an exploded, perspective view of the end effector of FIG. 1, according to the present disclosure.
Figure 12:
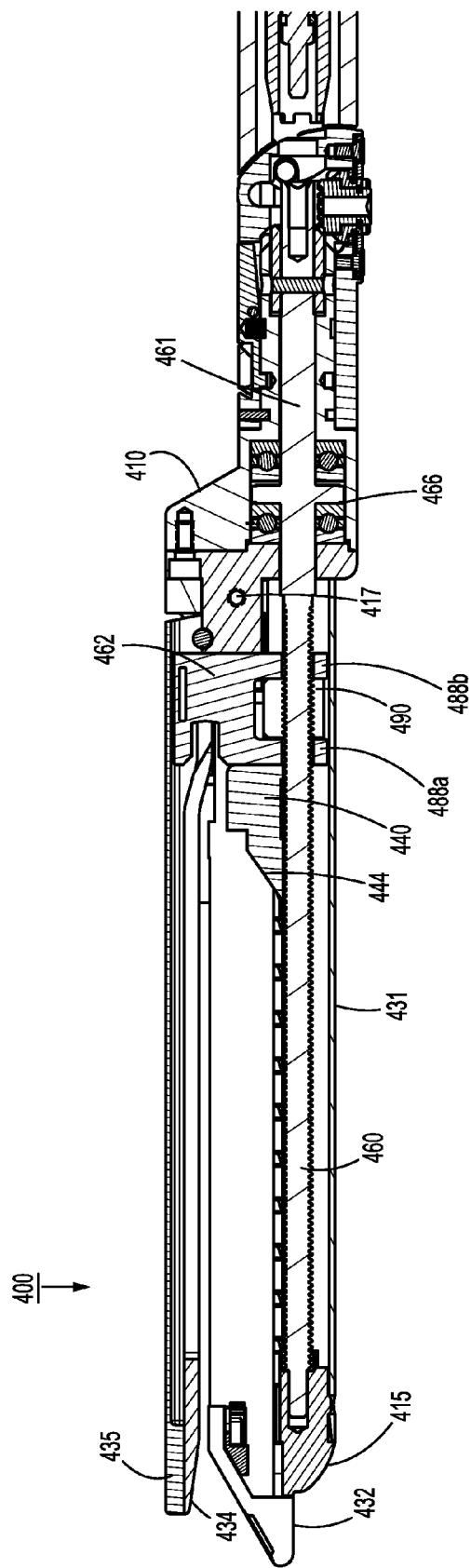
FIG. 12 is a side, cross-sectional view of the end effector of FIG. 1, according to the present disclosure.

FIGS. 11 and 12 illustrate components and operation of the end effector 400. End effector 400 includes a pair of jaw members, which include a cartridge assembly 432 and an anvil 434. Cartridge assembly 432 houses one or more fasteners 433 (FIG. 11) that are disposed therewithin and is configured to deploy the fasteners 433 upon firing of instrument 100. The anvil 434 is movably (e.g., pivotally) mounted to the end effector 400 and is movable between an open position, spaced apart from cartridge assembly 432, and a closed position wherein anvil 434 is in close cooperative alignment with cartridge assembly 432, to thereby clamp tissue.

Referring to FIG. 11, an exploded view of the end effector 400 is shown. The end effector 400 also includes a carrier 431 having an elongate channel 411, a base 412 and two parallel upstanding walls 414 and 416 which include several mounting structures, such as notches 439, for supporting the cartridge assembly 432 and the anvil 434. A longitudinal slot 413 extends through the elongate channel 411.

The carrier 431 also includes a plate cover 415 disposed on a bottom surface thereof. The plate cover 415 is configured to frictionally engage with channel 411 of the carrier 431 and functions to protect tissue from moving parts along the exterior of carrier 431. The carrier 431 also includes a pair of tabs 407 and 409 disposed at a proximal end of respective walls 414, 416, and being configures for coupling to a housing member 410 of end effector 400.

With continuing reference to FIG. 11, the distal portion of channel 411 supports the cartridge assembly 432 which contains the plurality of surgical fasteners 433 and a plurality of corresponding ejectors or pushers 437. End effector 400 includes an actuation sled 440 having upstanding cam wedges 444 configured to exert a fastener driving force on the pushers 437, which drive the fasteners 433 from cartridge assembly 432, as described in more detail below. Cartridge assembly 432 is maintained within channel 411 by lateral struts 436 which frictionally engage corresponding notches 439 formed in the upper surfaces of channel walls 414 and 416. These structures serve to restrict lateral, longitudinal, and elevational movement of the cartridge assembly 432 within channel 411.

A plurality of spaced apart longitudinal slots (not shown) extend through cartridge assembly 432 and accommodate the upstanding cam wedges 444 of actuation sled 440. The slots communicate with a plurality of pockets within which the plurality of fasteners 433 and pushers 437 are respectively supported. The pushers 437 are secured by a pusher retainer (not shown) disposed below the cartridge assembly 432, which supports and aligns the pushers 437 prior to engagement thereof by the actuation sled 440. During operation, as actuation sled 440 translates through cartridge assembly 432, the angled leading edges of cam wedges 444 sequentially contact pushers 437 causing the pushers to translate vertically within slots 446, urging the fasteners 434 therefrom. The cartridge assembly 432 also includes a longitudinal slot 485 to allow for a knife blade 474 to travel therethrough, as described in more detail below.

With continuing reference to FIG. 11, the end effector 400 includes an anvil cover 435 disposed over the anvil 434. The anvil cover 435 protects tissue from moving parts along the exterior of anvil 434. The anvil cover 435 includes opposed mounting wings 450 and 452 which are dimensioned and configured to engage detents 454 and 456 of the anvil 434, respectively. The mounting wings 450 and 452 function to align the anvil 434 with the cartridge assembly 432 during closure. The anvil 434 and the cover 435 are configured to remain in an open configuration until closed, as described in more detail below.

The anvil 434 is pivotally coupled to the carrier 431. The carrier 431 includes a pair of openings 421 and 422 formed in respective tabs 407, 409. The anvil cover 435 also includes a pair of opposed openings 457 and 459 found therein. A pivot pin 417, or a pair of pins, passes through the openings 421, 422, 457, and 459 allowing for pivotal coupling of the anvil 434 to the carrier 431.

As seen in FIG. 11, end effector 400 further includes an axial drive screw 460 for transmitting the rotational drive forces exerted by the flexible drive shaft 119 to actuation sled 440 during a stapling procedure. Drive screw 460 is rotatably supported in carrier 431 and includes a threaded portion 460a and a proximal end 461. The drive screw 460 is rotatably secured at a distal end of the cartridge 432 and includes one or more bearings 466 frictionally fitted about the proximal end 461. This allows the drive screw 460 to be rotated relative to the carrier 431. Proximal housing member 410 of the effector 400 is coupled to the proximal end of the carrier 431 via one or more bolts 412 and a spacer 410a. The housing member 410 includes a bore 414 defined therethrough that houses the proximal end 461 therein.

With confirmed reference to FIGS. 11 and 12, end effector 400 further includes a drive beam 462 disposed within carrier 431. The drive beam 462 includes a vertical support strut 472 and an abutment surface 476 which engages the central support wedge 445 of actuation sled 440. The drive beam 462 also includes a cam member 480 disposed on top of the vertical support strut 472. Cam member 480 is dimensioned and configured to engage and translate with respect to an exterior camming surface 482 of anvil 434 to progressively clamp the anvil 434 against body tissue during firing.

A longitudinal slot 484 extends through the anvil 434 to accommodate the translation of the vertical strut 472. This allows the cam member 480 to travel in between the cover 435 and anvil 434 during firing. In embodiments, the anvil cover 435 may also include a corresponding longitudinal slot (not shown) formed on an underside thereof and is secured to an upper surface of anvil 434 to form a channel therebetween.

The drive beam 462 includes a distal retention foot 488a and a proximal retention foot 488b, each having a bore 489a and 489b defined therethrough. The bores 489a and 489b may be either threaded or smooth to provide for travel along the drive screw 460 which passes therethrough. A travel nut 490 having a threaded bore 490a therethrough is disposed between the distal and proximal retention feet 488a and 488b. The drive screw 460 is threadably coupled to the travel nut 490 through the bore 490a, such that as the drive screw 460 is rotated, the travel nut 490 travels in a longitudinal direction along the longitudinal axis defined by the drive screw 460 and also engaging the feet 488a and 488b.

In use, as the drive screw 460 is rotated in a clock-wise direction, the travel nut 490 and the drive beam 462 travel in a distal direction closing the anvil 434 as the cam member 480 pushes down on the camming surface 482 thereof. The drive beam 462 also pushes the sled 440 in the distal direction, which then engages the pushers 437 via the cam wedges 444 to eject the fasteners 433. The drive beam 462 may be made of any suitable first material including, but not limited to, plastics, metals, and combinations thereof. The travel nut 490 may be made of any suitable second material also including, but not limited to, plastics, metals, and combinations thereof. The first and second materials may be either same or different. In embodiments, the drive beam 462 may include a single retention foot with a threaded bore defined therethrough, which is threadably coupled to the drive screw 460.

With reference to FIG. 11, the drive beam 462 also includes a knife blade 474 for dissecting the fastened tissue. The knife blade 474 travels slightly behind actuation sled 440 during a stapling procedure to form an incision between the rows of fastener. As the drive beam 462 is driven in the distal direction, the abutment surface 476 of the vertical strut 472 pushes the sled 440 in the distal direction to eject the fasteners 433 and simultaneously dissect tissue with the knife blade 474. The knife blade 474 and the drive beam 462 travel through the longitudinal slots 484 and 485. The drive beam 462 closes the anvil as it is driven in the distal direction and also pushes the sled 440, which, in turn, ejects the fasteners 433 ahead of the knife blade 474. As the fasteners 433 are ejected they are deformed again the tissue-contacting (e.g., underside) surface of the anvil 434 having a plurality of anvil pockets (not shown).

Figure 15:
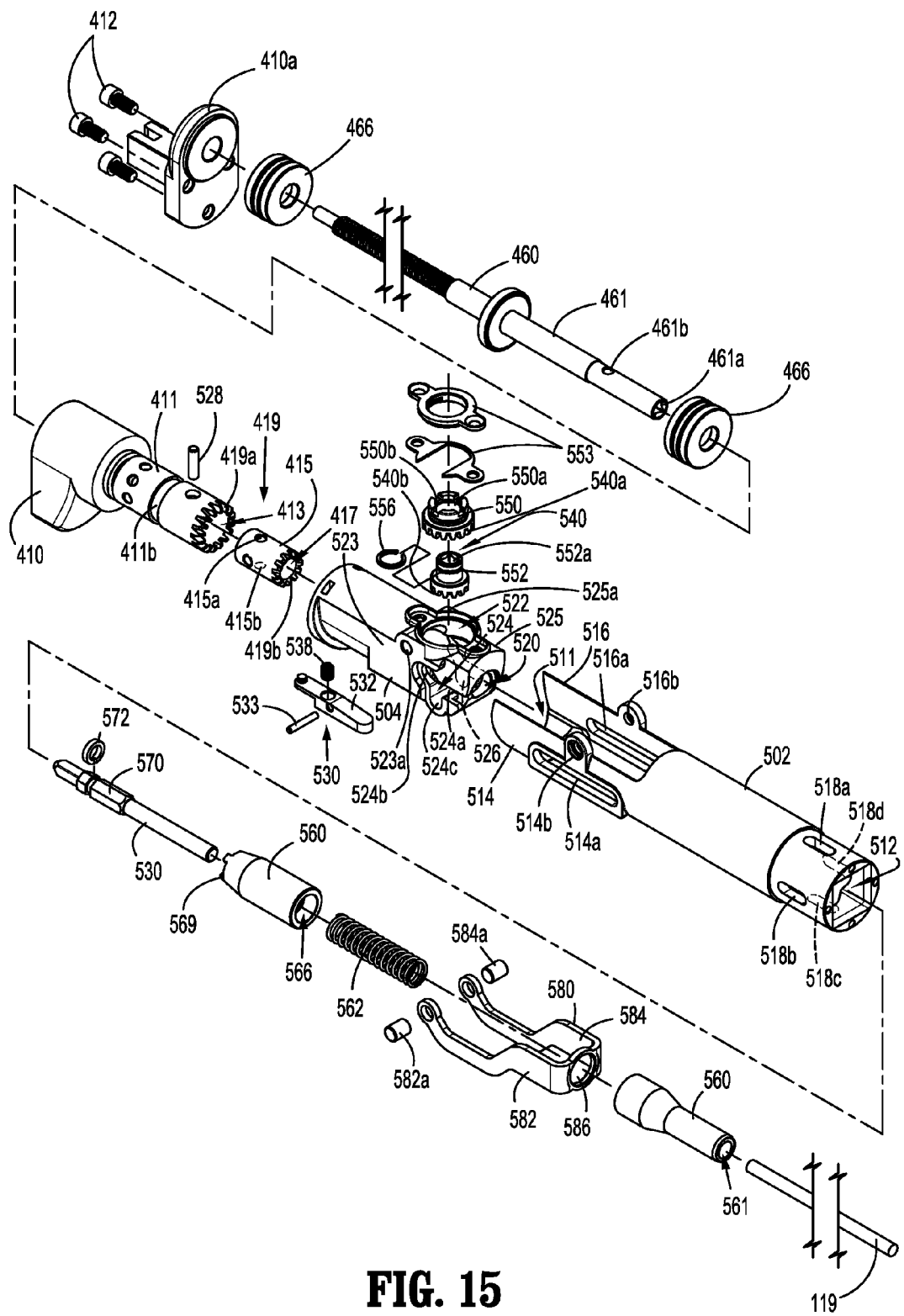
FIG. 15 is an exploded, perspective view of the pivoting linkage of FIG. 13, according to the present disclosure.

With respect to FIGS. 13-16, the pivoting linkage 500 includes a rigid proximal joint member 502 and a rigid distal joint member 504 coupled to the end effector 400. The proximal and distal members 502 and 504 are pivotally coupled to each other. Referring to FIG. 15, an exploded view of the pivoting linkage 500 is shown. The proximal joint member 502 also includes two parallel upstanding walls 514 and 516 defining an elongate channel 511 at its distal end that transitions into a longitudinal lumen 512 at its proximal end. Each of the walls 514 and 516 includes an elongate slot 514a and 516a defined therein and an opening 514b and 516b, respectively. The proximal joint member 502 also includes anchor points 518a, 518b, 518c, 518d disposed at a proximal end thereof. The anchor points 518a, 518b, 518c, 518d are coupled to the distal ends of the cables 205a, 205b, 205c, 205d thereby securing the segments 206 of the flexible shaft 202 between the proximal joint member 502 and the rigid portion 204.

The distal joint member 504 includes a longitudinal lumen 520 defined therethrough that connects to a transverse lumen 522 that is transverse to the longitudinal lumen 520. The distal joint member 504 may include a pair of opposing walls 523 and 525 configured to fit between the walls 514 and 516 of the proximal joint member 502. The distal joint member 504 has at least one cam slot defined in the walls 523 and 525 at a proximal end of the distal joint member. For example, cam slots 524 and 526 are defined within the walls 523 and 525 at a proximal end of the distal joint member 504. The distal joint member 504 further includes a pair of openings 523a and 525a defined through the distal joint member 504. A pair of mechanical fasteners, such as pins, rivets, and the like, pass through each the openings 523a, 525a of the distal joint member 504 and corresponding openings 514b and 516b of the proximal joint member 502 allowing for pivotal coupling of the distal joint member 504 to the proximal joint member 502 (e.g., via rivets, stamping, crimping, etc.).

Figure 16:
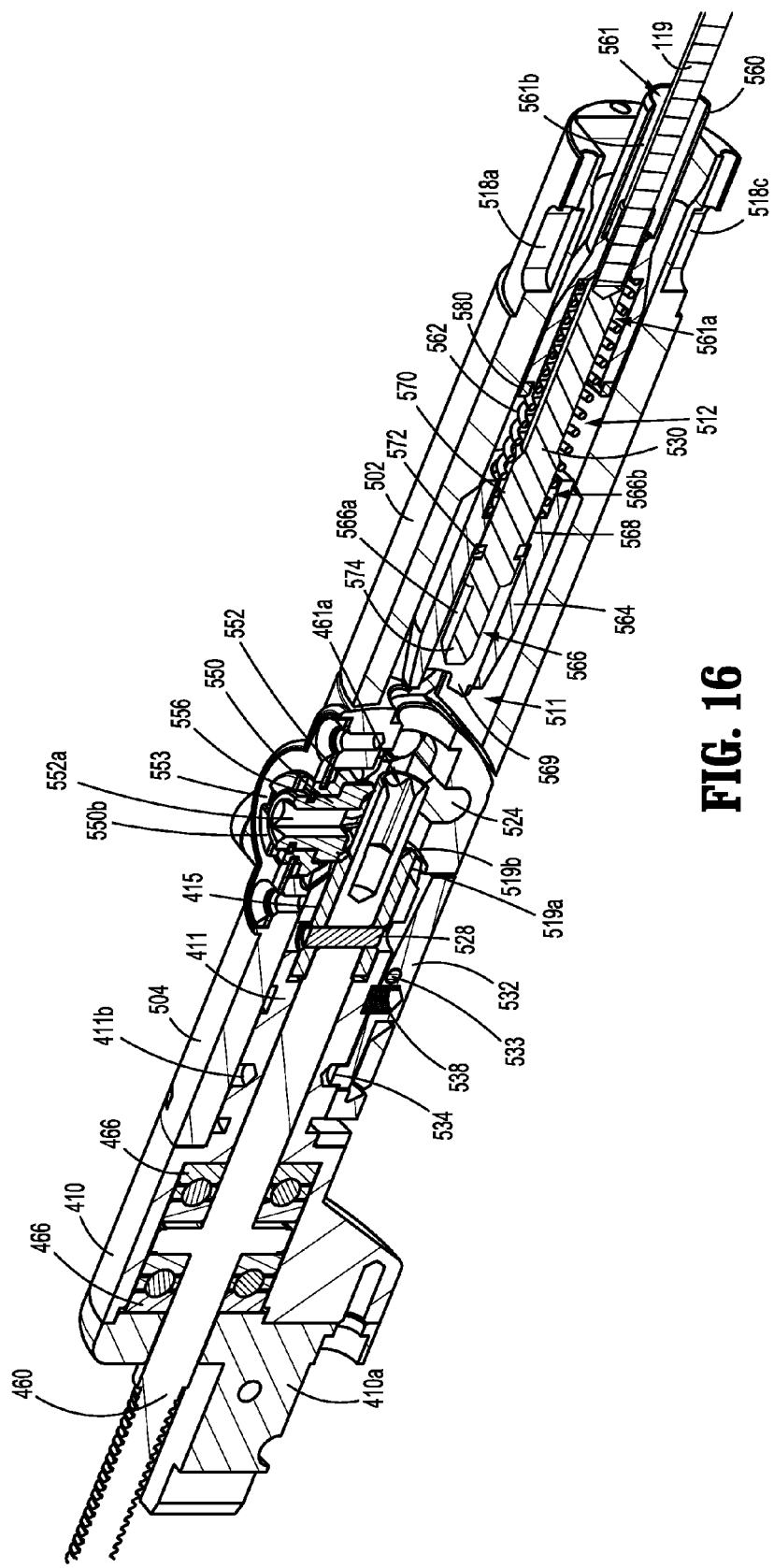
FIG. 16 is a perspective, cross-sectional view of the pivoting linkage of FIG. 13 in an aligned configuration with a drive shaft disengaged an according to the present disclosure.

With continuing reference to FIGS. 15 and 16, the housing member 410 further includes an outer rotational engagement portion 411. The outer rotational engagement portion 411 has a substantially cylindrical shape defining a longitudinal lumen 413 therethrough. The engagement portion 411 also includes an inner rotational engagement portion 415 disposed at a proximal end thereof and within the lumen 413. Similarly to the engagement portion 411, the engagement portion 415 has a substantially cylindrical shape defining a longitudinal lumen 417 therethrough. The proximal end 461 of the drive screw 460 extends through the housing member 410 such that the proximal end 461 of the drive screw 460 extends through the lumens 413 and 415 of the outer rotational engagement portion 411 and inner rotational engagement portion 415, respectively, as well as the lumen 520 of the distal joint member 504. The proximal end 461 of the drive screw 460 includes a female opening 461a having a complementary mating surface configured and dimensioned to mechanically interface with a drive shaft 530 as described in further detail below.

The engagement portion 415 of the housing member 410 is fixedly coupled to the proximal end 461 of the drive screw 460 and includes a pair of openings 415a, 415b defined in the cylindrical walls thereof. The drive screw 460 includes a proximal transverse lumen 461b therethrough. The proximal transverse lumen 461b is aligned with the openings 415a, 415b of the engagement portion 415 such that a pin 528 is frictionally fitted therethrough thereby securing the drive screw 460 to the engagement portion 415. In embodiments, the engagement portion 415 may be secured to the proximal end 461 of the drive screw 460 using any suitable methods, such as, mechanical fasteners, adhesives, and the like. In further embodiments, the engagement portion 415 may be formed integrally with the drive screw 460. The inner rotational engagement portion 415 may freely rotate within the outer rotational engagement portion 411. This configuration allows the drive screw 460 along with the engagement portion 415 to be rotated relative to the outer rotational engagement portion 411 and relative to the housing member 410.

The end effector 400 includes a primary gearing assembly 419. The gearing assembly 419 includes a first gear 419a and a second gear 419b defined at proximal ends of the engagement portions 411 and 415, respectively. The gears 419a and 419b are configured and dimensioned as miter or bevel gears and may be formed by chamfering the proximal edges of the engagement portions 411 and 415, respectively.

As described in further detail below, engagement of the gear 419a allows for rotation of the engagement portion 411 along with the housing member 410 and the end effector 400 about the longitudinal axis B-B relative to the pivoting linkage 500. Additionally, engagement of the gear 419b allows for rotation of the engagement portion 415 along with the drive screw 460 to close the anvil 434, eject the fasteners 433, and/or cut tissue as described above.

In embodiments, the end effector 400 may be removably coupled to the pivoting linkage 500. As shown in FIGS. 15 and 16, the distal joint member 504 includes a latch assembly 530 that is adapted to engage a groove 411*b* on the surface of outer rotational engagement portion 411. The latch assembly 530 includes a lever 532 pivotally coupled via a pin 533 to the outer surface of the distal joint member 504. The lever 532 includes a knob 534 configured and dimensioned for engaging the groove 411*b* of outer rotational engagement portion 411 and a cavity 536 for housing a spring 538, which biases the lever 532, and in turn, the knob 534 into engagement with the groove 411*b* of the outer rotational engagement portion 411. The groove 411*b* extends along the entire outer circumference of the outer rotational engagement portion 411, such that when the knob 534 is disposed within the groove 411*b*, the end effector 400 is secured to the pivoting linkage 500 while still allowing for rotation of the end effector 400 relative to the pivoting linkage 500. During insertion and/or ejection of the end effector 400 from the pivoting linkage 500, the lever 532 is depressed to pull the knob 534 from engagement with the groove 411*b* of the outer rotational engagement portion 411.

With continuing reference to FIGS. 15 and 16, the distal joint member 504 also includes secondary outer and secondary inner engagement members 550 and 552, respectively. The secondary outer engagement member 550 is rotationally disposed within the lumen 522 of the distal joint member 504. The secondary outer engagement member 550 defines a lumen 550*a* therethrough and the secondary inner engagement member 552 is configured and dimensioned to rotate therein. A bushing 556 is disposed about the outer circumference of the secondary inner engagement member 552 acting as a buffer between the engagement members 550 and 552 allowing for rotation of the secondary outer and secondary inner engagement members 550 and 552 relative to each other and relative to the distal joint member 504.

With respect to FIG. 16, the secondary outer engagement member 550 includes a mating surface 550*b* configured and dimensioned to mechanically interface with a rotation link 564 as described in further detail below. The secondary inner engagement member 552 also includes a mating surface 552*a* configured and dimensioned to mechanically interface with the drive shaft 530 as described in further detail below.

With continuing reference to FIGS. 15 and 16, the distal joint member 504 also includes a secondary gearing assembly 540. The secondary gearing assembly 540 includes a first gear 540*a* and a second gear 540*b*. The first gear 540*a* and the second gear 540*b* are configured and dimensioned as miter or bevel gears for engaging the first gear 419*a* and the second gear 419*b*, respectively. The gears 540*a* and 540*b* are disposed on the opposite ends from the mating surfaces 550*a* and 552*a* of the secondary outer and secondary inner engagement members 550 and 552, respectively.

As shown in FIG. 16, the proximal end of the engagement portion 415 of housing member 410 is disposed proximally of the proximal end of the outer rotational engagement portion 411, such that the internally disposed second gear 419*b* extends outside the first gear 419*a*. Similarly, the internally disposed gear 540*b* of the secondary inner engagement member 552 extends past the gear 540*a* of the secondary outer engagement member 550. The secondary outer and secondary inner engagement members 550 and 552 are secured within the lumen 522 of the distal joint member 504 by one or more washers 553. In particular the washers 553 abut the secondary outer engagement member 550, which in turn, abuts the secondary inner engagement member 552 thereby interlocking the first gear 540*a* and the second gear 540*b* with the first gear 419*a* and the second gear 419*b*, respectively.

Figure 18:
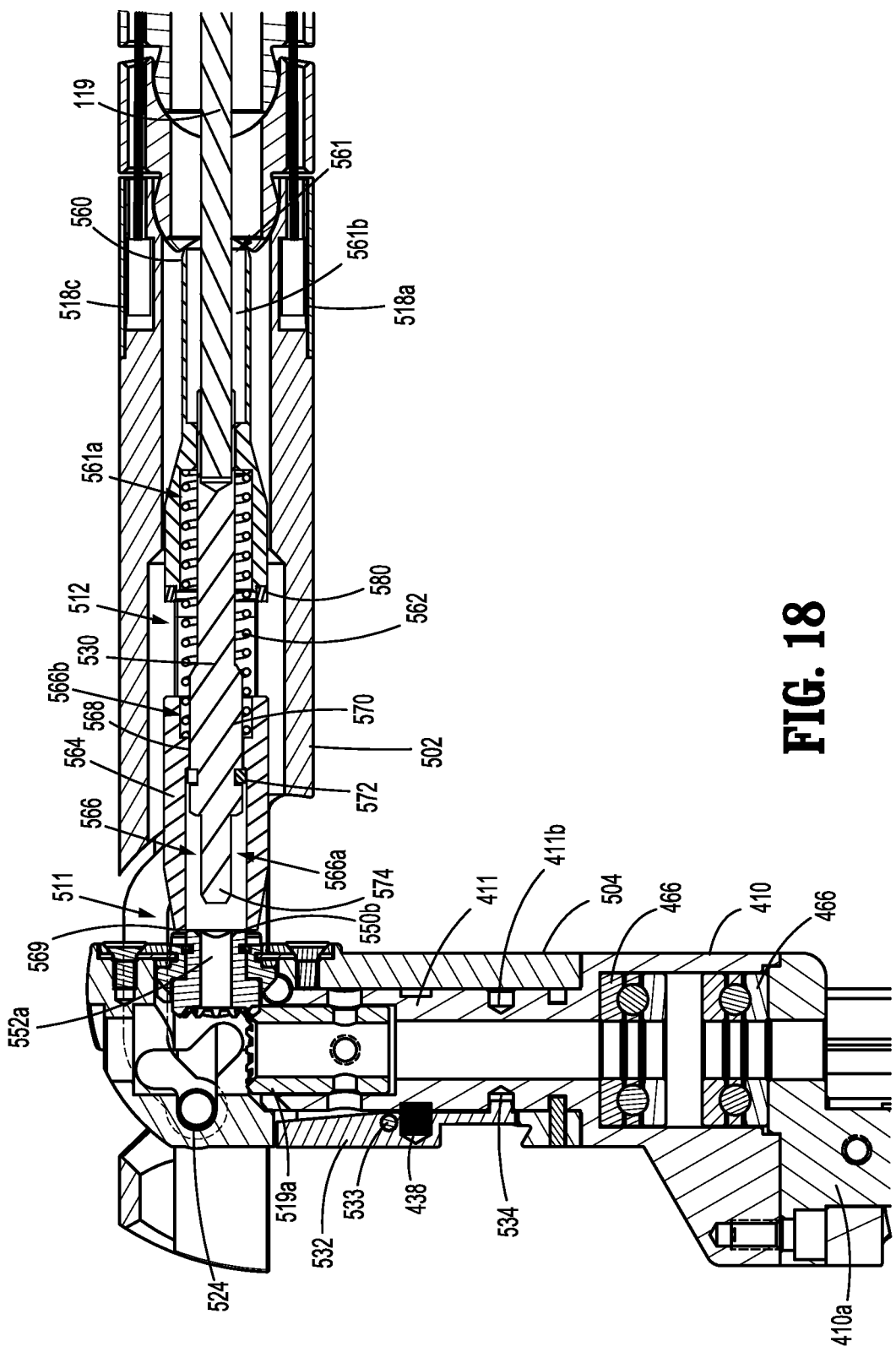
FIG. 18 is a perspective, cross-sectional view of the pivoting linkage of FIG. 13 in a pivoted configuration with the drive shaft disengaged an according to the present disclosure.
Figure 19:
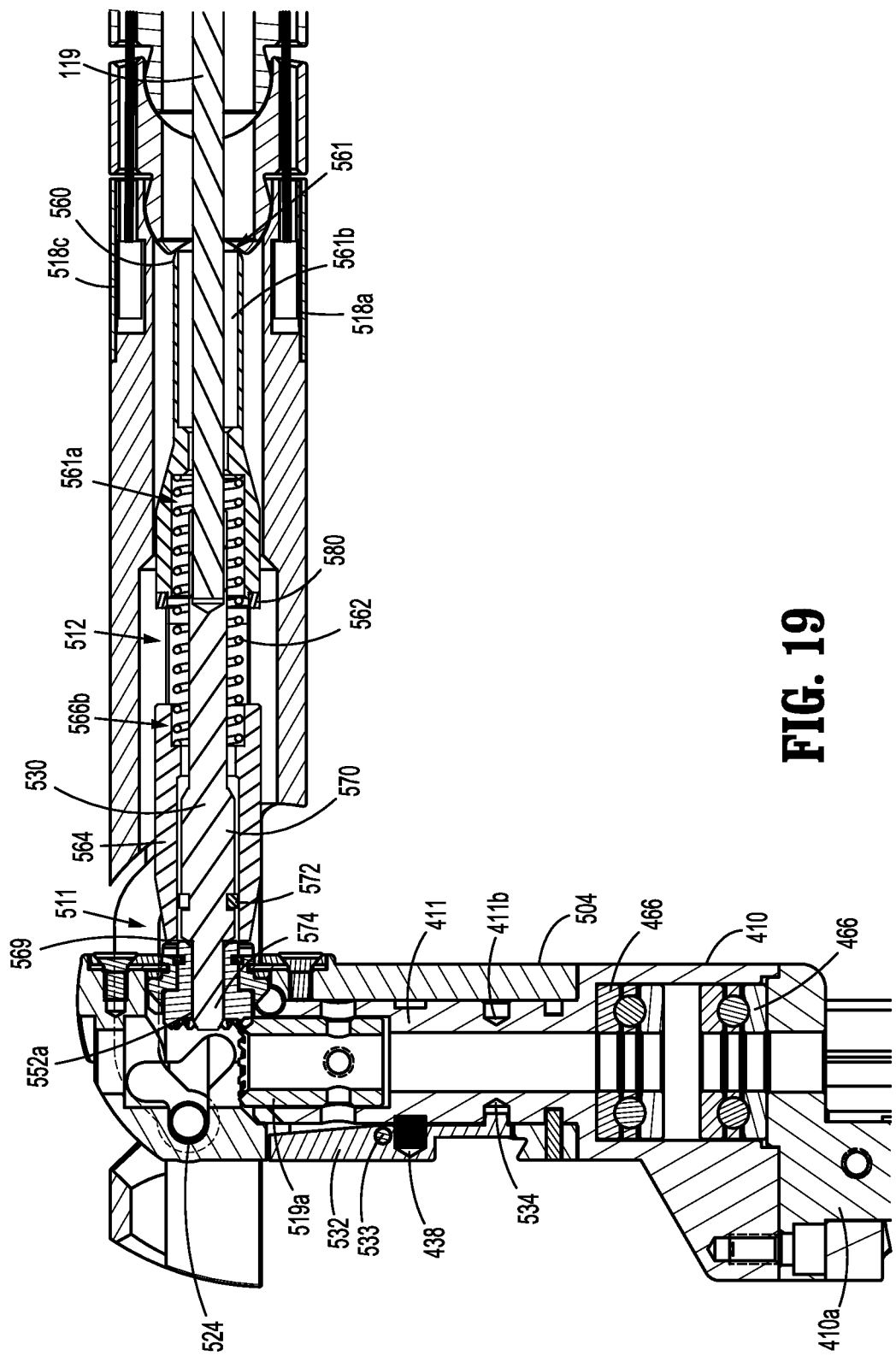
FIG. 19 is a perspective, cross-sectional view of the pivoting linkage of FIG. 13 in the pivoted configuration with the drive shaft engaged an according to the present disclosure.

With continued reference to FIGS. 15 and 16, the proximal joint member 502 includes a push rod 560 disposed within the lumen 512 of joint member 502. The push rod 560 is configured to slidingly move within the lumen 512 of joint member 502 and is configured and dimensioned to engage the most distal segment 206 of joint member 502. In embodiments, the distal segment 206 of joint member 502 may include a cavity configured and dimensioned to engage the proximal end of the push rod 560 as shown in FIGS. 18 and 19. The push rod 560 is moved in the distal direction by tensioning cables 205*a*, 205*b*, 205*c*, 205*d* to approximate the pivoting linkage 500 to the distal segment 206, which in turn, advances the push rod 560 into the lumen 512 of joint member 502.

The push rod 560 defines a longitudinal lumen 561 to allow for passage of the drive shaft 119 therethrough. The lumen 561 of push rod 560 also includes a distal portion 561*a* and a proximal portion 561*b*. The drive shaft 530 is coupled to the flexible drive shaft 119 within the lumen 561 of push rod 560. In particular, the drive shaft 119 is disposed within the proximal portion 561*b* of the lumen 561 of push rod 560 and the drive shaft 530 is disposed within the distal portion 561*a* of lumen 561 establishing a coupling therebetween.

The distal portion 561*a* of the lumen 561 has a larger diameter than the proximal portion 561*b* and is sufficient to accommodate a spring 562 disposed over the drive shaft 530. The spring 562 is biased between the push rod 560 and a rotation link 564. The rotation link 564 has a substantially cylindrical shape and defines a longitudinal lumen 566 to allow for passage of the drive shaft 530 therethrough. Similarly to the push rod 560, the rotation link 564 is also configured to slidingly move within the lumen 512 as well as to rotate therein. The lumen 566 of rotation link 564 also includes a distal portion 566*a* and a proximal portion 566*b*. The distal and proximal portions 566*a* and 566*b* of lumen 566 include a ridge 568 therebetween which provides a seat for the spring 562. The rotation link 564 also includes a gear 569 at its distal end that is configured and dimensioned to mechanically interface with the mating surface 550*b* of the engagement member 550.

The drive shaft 530 is disposed within the lumen 566 of rotation link 564 and is configured to slidingly move and/or to rotate therein. The drive shaft 530 is also disposed within the spring 562, without contacting the spring 562, allowing the drive shaft 530 to move independently inside thereof. The distal end of the drive shaft 119 and the proximal end of the drive shaft 530 include complementary mating surfaces, such that rotation and longitudinal movement of the drive shaft 119 is transferred to the drive shaft 530.

The drive shaft 530 also includes an intermediate portion 570 that provides a complementary mating surface to the ridge 568. This allows for transfer of rotational motion of the drive shaft 530 to the rotation link 564. The intermediate portion 570 of drive shaft 530 also includes a bushing 572, which is disposed about the outer circumference of the engagement intermediate portion 570 acting as a buffer between the drive shaft 530 and the inner walls of the rotation link 564 allowing for rotation of the drive shaft 530 within the rotation link 564 when the intermediate portion 570 of drive shaft 530 and the ridge 568 of rotation link 564 are disengaged. The bushing 572 also acts as a stop member, preventing proximal movement of the drive shaft 530 relative to the rotation link 564 since bushing 572 is configured and dimensioned to come in contact with the ridge 568 of rotation link 564 as the drive shaft 530 is moved in the proximal direction.

There is a camming mechanism associated with the pivoting linkage. With reference to FIGS. 14-16, a substantially U-shaped clevis 580 is associated with the proximal joint member 502. The clevis 580 has first and second longitudinal arms 582 and 584 extending distally from an opening 586. The clevis 580 is disposed within the lumen 512 of proximal joint member 502. In embodiments, the arms 582 and 584 may extend outside the proximal joint member 502 as shown in FIGS. 13 and 14. The U-shaped structure of the clevis 580 along with the opening 586 allows for longitudinal travel of the drive shaft 530 therethrough.

Each of the longitudinal arms 582 and 584 includes a camming pin 582a and 584a at distal ends thereof. The camming pins 582 and 584 are disposed within the slots 514a and 516a, respectively, of the proximal joint member 502. The clevis 580 is moved distally by the push rod 560 as it is engaged by the distal segment 206. The slots 514a and 516a of proximal joint member 502 maintain the travel of the clevis 580 along the longitudinal axis B-B.

The camming pins 582a and 584a are also disposed within the cam slots 524 and 526 of distal joint member 504 as shown in FIGS. 15 and 18, respectively. Each of the cam slots 524 and 526 of distal joint member 504 includes a first portion 524a, 526a, a second portion 524b, 526b, and a third portion 524c, 526c, respectively. For simplicity, only the cam slot 526 and first, second, and third portions 526a, 526b, 526c, are discussed below since the structure and operation of the cam slot 524 and first, second, and third portions 524a, 524b, 524c is substantially similar thereto.

The first portion 526a of cam slot 526 is substantially aligned with longitudinal axis "B-B" defined by end effector 400. The third portion 526c of cam slot 526 extends substantially perpendicularly to the longitudinal axis "B-B." The second portion 526b of cam slot 526 is angled at an obtuse angle with respect to the first portion 526a (e.g., the longitudinal axis "B-B") and the second portions 524b. In embodiments, the second portion 526b is angled at about 45° relative to the longitudinal axis "B-B." The first portion of the cam slot extends at an angle with respect to the second portion and the third portion of the cam slot. For example, the first, second, and third portions of the cam slots have a Y-shaped configuration as seen in FIGS. 20 through 24. It is contemplated that the cam slot can have two portions that are angled with respect to one another, or more than three portions that are angled with respect to one another.

As shown in FIG. 6, the end effector 400 may be articulated with respect to the rigid portion 204 of the shaft assembly 200 via the flexible shaft 202 as well as pivoted with respect to the flexible shaft 202 via the joint members 502 and 504 about the openings 514b, 516b and 523a, 525a, respectively. The end effector 400 may be pivoted between an aligned (e.g., not pivoted) configuration in which the longitudinal axis "B-B" defined by the end effector 400 is aligned with the longitudinal axis "C-C" defined by the proximal joint member 502, as shown in FIG. 1, and a pivoted configuration in which the longitudinal axis "B-B" is perpendicular to the longitudinal axis "C-C," as shown in FIG. 6.

The flexible drive shaft 119 allows for operation of the end effector 400 regardless of the articulation imparted on the flexible shaft 202. The flexible shaft 202 may be articulated in any desired direction as described above with respect to FIGS. 7-10. The end effector 400 may be actuated (e.g., approximation of the cartridge assembly 432 and the anvil 434 and/or eject the fasteners 433) in either the aligned (e.g., not pivoted) configuration or the pivoted configuration.

Figure 17:
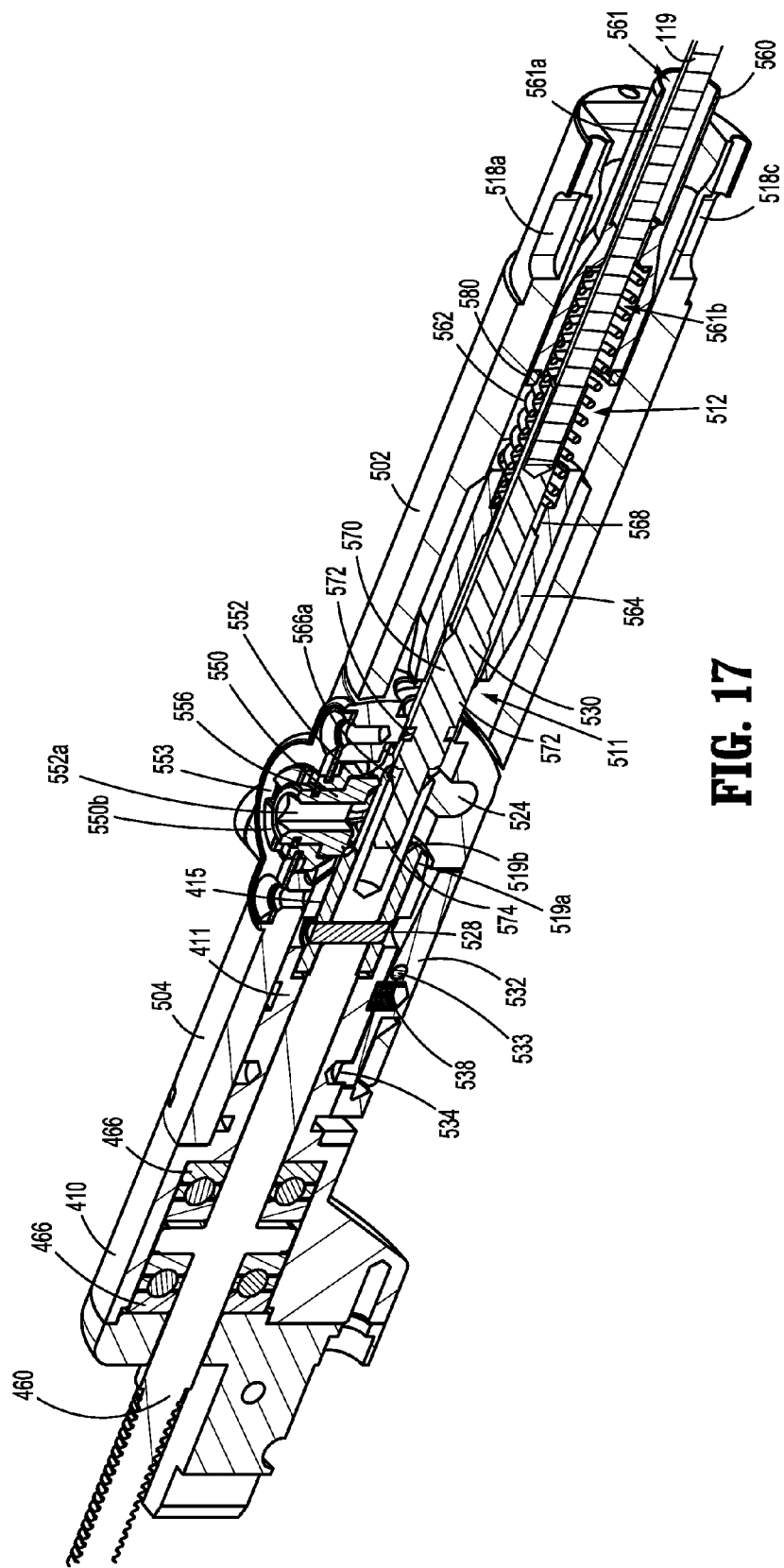
FIG. 17 is a perspective, cross-sectional view of the pivoting linkage of FIG. 13 in the aligned configuration with the drive shaft engaged an according to the present disclosure.

Turning now to FIGS. 16 and 17, operation of the end effector 400 in the aligned configuration, e.g., the joint members 502 and 504 are aligned along the longitudinal axis "B-B," is shown and described. In the aligned configuration, the push rod 560 is not engaged by the distal segment 206, as that would effect articulation of the end effector 400 via the joint members 502 and 504, as described below with respect to FIGS. 18-24.

Once the end effector 400 is articulated in a desired position with respect to the shaft assembly 200, the end effector 400 may be actuated to clamp and/or seal tissue. To effect actuation, the flexible drive shaft 119 is extended in the distal direction, which in turn, pushes the drive shaft 530 into engagement with the opening 461a of the drive screw 460. The drive shaft 530 moves in a distal direction independently of the push rod 560, the spring 562, and the rotation link 564 as described above. Once the drive shaft 530 is engaged with the drive screw 460, the flexible drive shaft 119 is rotated about the longitudinal axes "A-A" and/or "C-C" depending on the angle of articulation thereof. Rotation of the drive shaft 119 in a clockwise direction effects rotation of the drive shaft 530 in the same direction, which in turn, rotates the drive screw 460 thereby clamping and/or compressing tissue between the cartridge assembly 432 and the anvil 434 as described above with respect to FIGS. 11 and 12.

Turning now to FIGS. 20-24, the pivoting of the end effector 400 with respect to the flexible shaft 202 via the joint members 502 and 504 about the openings 514b, 516b and 523a, 525a, respectively, is shown and described.

Initially, as described above with respect to FIGS. 7-10, the distal segment 206 of flexible shaft 202 is pushed toward the proximal joint member 502 via tensioning of the cables 205a, 205b, 205c, 205d, which in turn, pushes the push rod 560 longitudinally in a distal direction. The push rod 560 engages the clevis 580, which then engages the spring 562 thereby biasing the rotation link 564.

Figure 20:
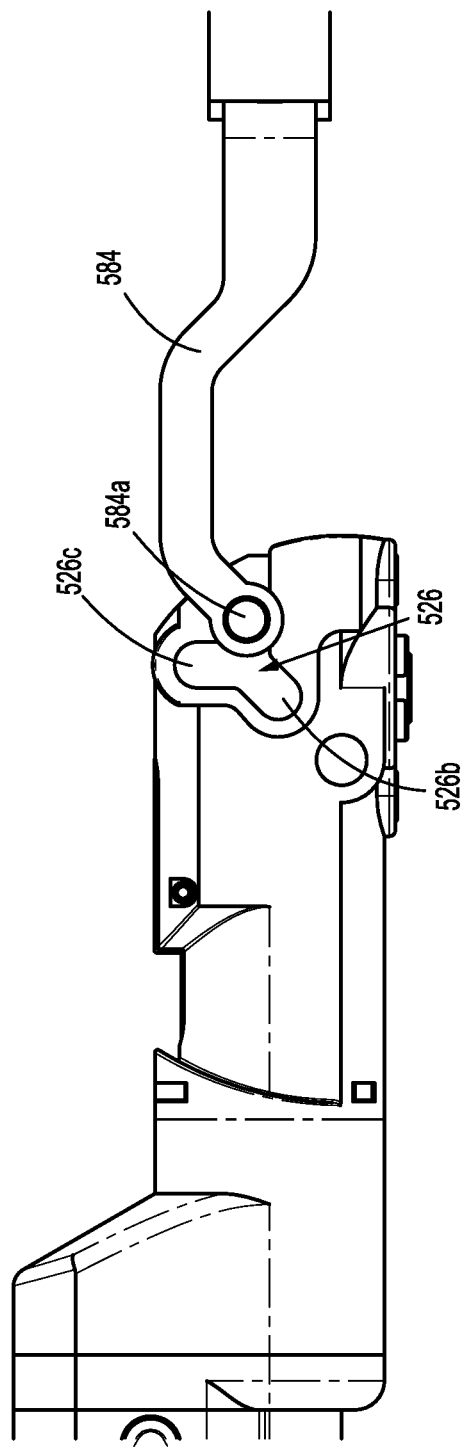
FIG. 20 is a side, partially-exploded view of the pivoting linkage of FIG. 13 in the aligned configuration according to the present disclosure.
Figure 21:
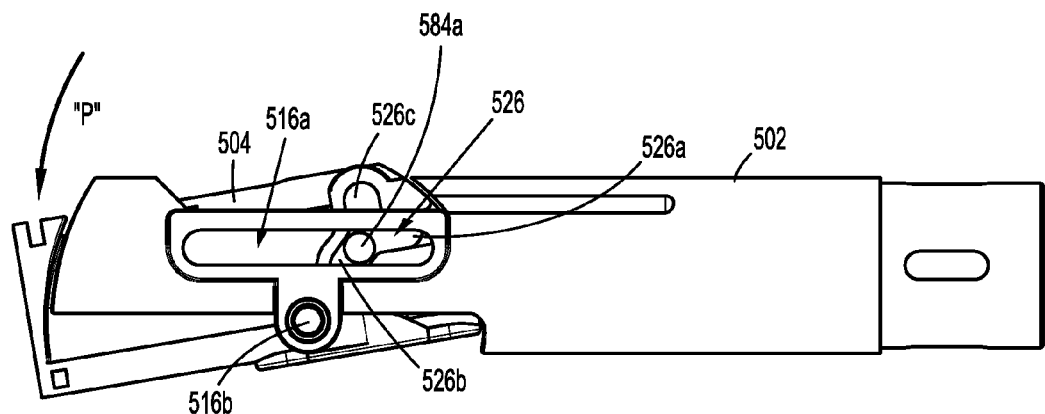
FIG. 21 is a side view of the pivoting linkage of FIG. 13 transitioning from the aligned configuration to the pivoted configuration with a camming pin engaging a second portion of a cam slot according to the present disclosure.

Longitudinal movement of clevis 580 longitudinally moves the cam pins 582a, 584a, through elongate slots 514a, 516a of proximal member 502 and through first portions 524a, 526a of cam slots 524 and 526 of the distal member 504 as shown in FIGS. 20 and 21. As shown in FIG. 21, the cam pins 582a, 584a are longitudinally moved through first portions 524a, 526a of cam slots 524, 526 until cam pins 582a, 584a contact or otherwise operatively engage shoulders between first portions 524a, 526a and second portions 524b, 526b of cam slots 524, 526. This causes the proximal joint member 502 to begin to rotate about the openings 514b, 516b and 523a, 525a, as indicated by arrow "P".

Figure 22:
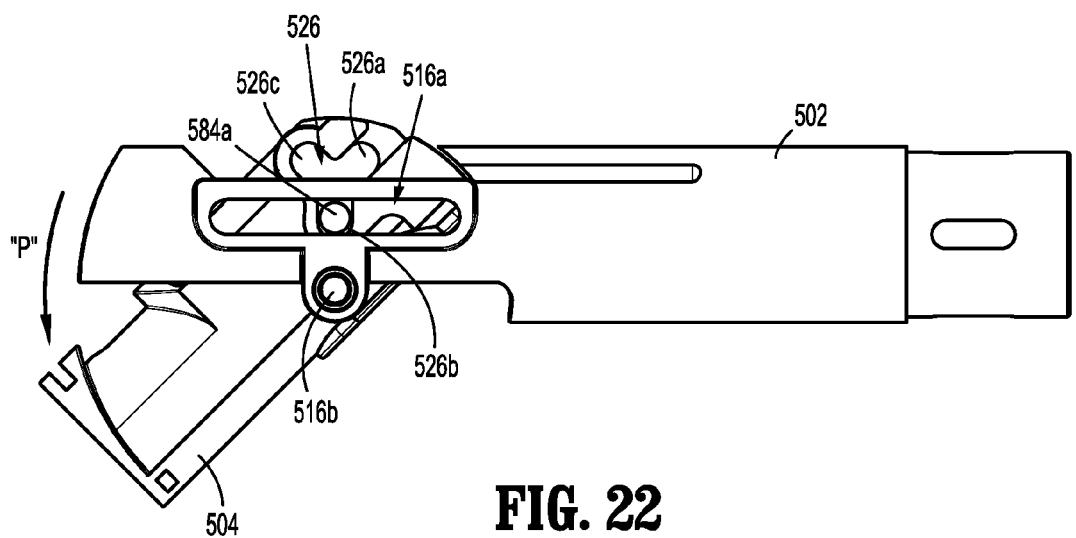
FIG. 22 is a side view of the pivoting linkage of FIG. 13 transitioning from the aligned configuration to the pivoted configuration with the camming pin engaged in the second portion of the cam slot according to the present disclosure.

With respect to FIG. 22, upon continued longitudinal movement of cam pins 582a, 584a through elongate slots 514a, 516a, cam pins 582a, 584a enter second portions 524b, 526b of cam slots 524, 526 and cause proximal joint member 502 to be in a half-way pivoted configuration.

Figure 23:
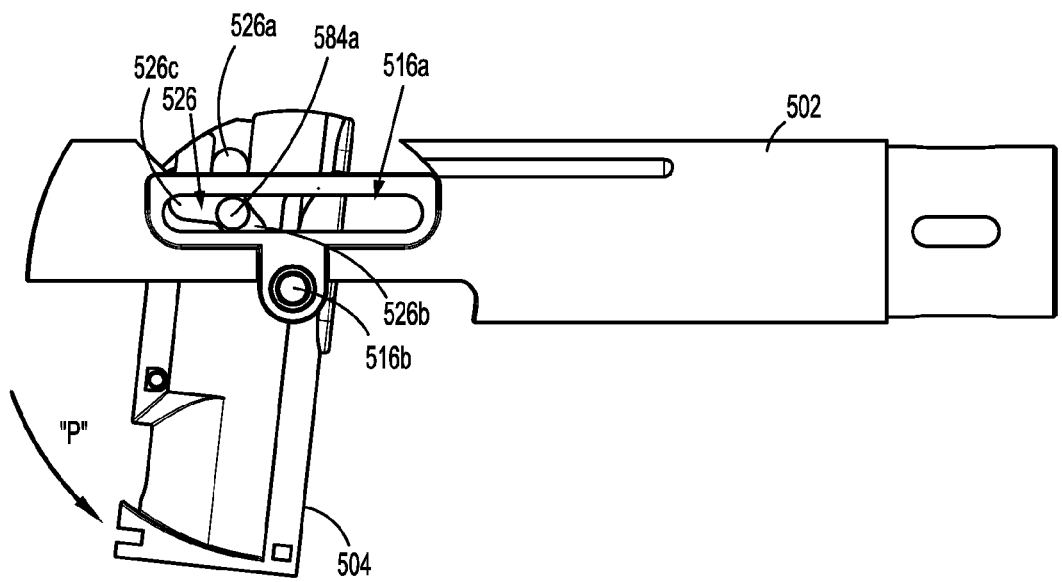
FIG. 23 is a side view of the pivoting linkage of FIG. 13 transitioning from the aligned configuration to the pivoted configuration with the camming pin engaging a third portion of the cam slot according to the present disclosure.

With respect to FIG. 23, continued longitudinal movement of cam pins 582a, 584a through elongate slots 514a, 516a, moves the cam pins 582a, 584a from the second portions 524b, 526b of cam slots 524, 526 until the cam pins 582a, 584a contact or otherwise operatively engage shoulders between second portions 524b, 526b and third portions 524c, 526c of cam slots 524, 526. This causes the proximal joint member 502 to continue to rotate about the openings 514b, 516b and 523a, 525a, as indicated by arrow "P".

Figure 24:
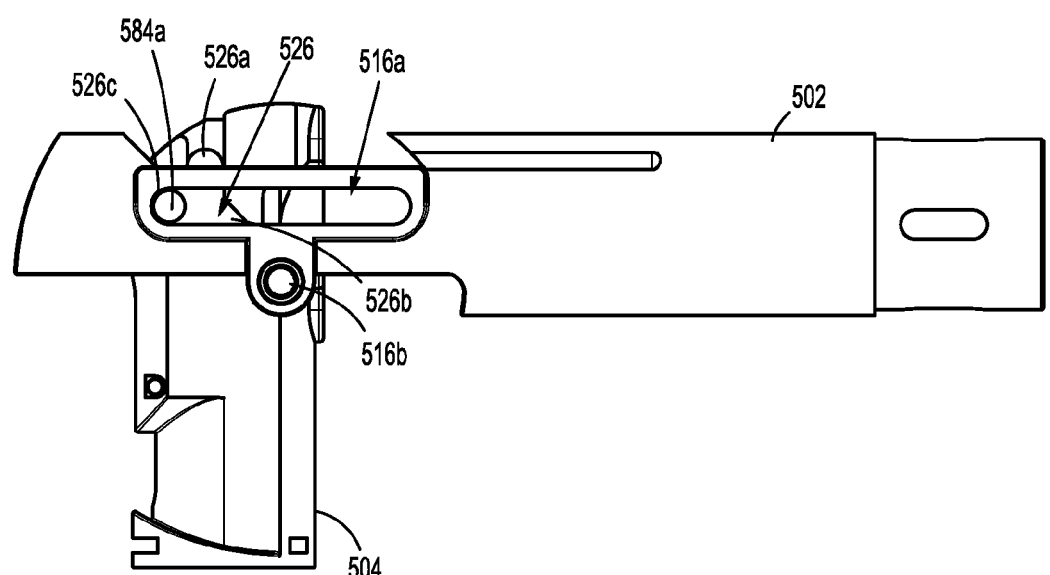
FIG. 24 is a side view of the pivoting linkage of FIG. 13 in the pivoted configuration with the camming pin engaged in the third portion of the cam slot according to the present disclosure.

As shown in FIG. 24, continued longitudinal movement of cam pins 582a, 584a through elongate slots 514a, 516a, causes the distal portion 504, along with the end effector 400, to rotate, about the openings 514b, 516b and 523a, 525a to the pivoted configuration. Continued longitudinal movement of cam pins 582a, 584a through elongate slots 514a, 516a, engages the third portions 524c, 526c of cam slots 524, 526. When applicator end effector 400 has been rotated into the pivoted configuration, second portion 524b, 526b of cam slots 524, 526 is substantially axially aligned with the longitudinal axis of elongate slots 514a, 516a. Accordingly, with end effector 400 in the pivoted configuration, cam pins 582a, 584a may move through second portion 524b, 526b of cam slots 524, 526.

With reference to FIG. 18, once the end effector 400 and the distal joint member 504 are in the articulated configuration, the rotation link 564 is engaged with the end effector 400. In the articulated configuration, the end effector 400 may be rotated about the longitudinal axis "B-B." As described above, the push rod 560 is moved in the distal direction to engage the clevis 580 in order to pivot the distal joint member 504 along with the end effector 400 with respect to the proximal joint member 502. Distal movement of the push rod 560 also engages the spring 562 biasing the rotation link 564, which engages the rotation link 564 with the outer engagement member 550. In particular, the gear 569 of the rotation link 564 meshes with the mating surface 550b of the outer engagement member 550.

The drive shaft 530 is mechanically engaged with the rotation link 564 via the intermediate portion 570 that provides a complementary mating surface to the ridge 568, such that rotation of the drive shaft 530, in turn, rotates the rotation link 564. Rotation of the drive shaft 119 in a clockwise direction effects rotation of the 530 in the same direction, which then rotates the rotation link 564. The engagement member 550 is also rotated since it is coupled to the rotation link 564 and is then transferred to the engagement portion 411. In particular, the first gear 540a of the engagement member 550 interlocks with the second gear 419a of the engagement portion 411. Rotation of the engagement portion 411 also rotates the end effector 400 about the longitudinal axis "B-B" with respect to the drive screw 460 since the drive screw 460 is rotatably coupled to the end effector 400 via the bearings 466.

As shown in FIG. 19, the drive shaft 530 may be advanced in the distal direction to engage the drive screw 460 to clamp and/or seal tissue between the cartridge assembly 432 and the anvil 434 as described above with respect to FIGS. 11 and 12. In particular, to effect actuation, the flexible drive shaft 119 is extended in the distal direction. This moves the drive shaft 530 in the distal direction, disengaging the intermediate portion 570 of the drive shaft 530 from the complementary mating surface of the ridge 568 of the rotation link 564. This allows the drive shaft 530 to be rotated within the rotation link 564, such that rotation of the drive shaft 530 is used to rotate the drive screw 460 to clamp and/or seal tissue between the cartridge assembly 432 and the anvil 434 rather than rotate the end effector 400 as described above.

As the drive shaft 530 is extended in the distal direction, the drive shaft 530 is disengaged from the rotation link 564 and is instead engaged with the mating surface 552a of the engagement member 552. The engagement member 552 is mechanically connected to the engagement portion 415 that is, in turn, coupled to the drive screw 460. In particular, the second gear 540b of the engagement member 552 interlocks with the second gear 419b of the engagement portion 415.

Once the drive shaft 530 is engaged with engagement member 552, the flexible drive shaft 119 is rotated. Rotation of the drive shaft 119 in a clockwise direction effects rotation of the drive shaft 530 in the same direction, which then rotates the engagement member 552. Rotation of the engagement member 552 is transferred to the engagement portion 415, which rotates the drive screw 460 along therewith. Rotation of the drive screw 460 effectuates clamping and/or compressing of tissue as described above with respect to FIGS. 11 and 12.

The pivoting process may be reversed to return the end effector 400 along with the distal joint member 504 into alignment with the proximal joint member 502. Initially, the rotation link 564 and the drive shaft 530 are disengaged from the end effector 400. The flexible drive shaft 119 is withdrawn in the proximal direction thereby pulling along therewith the drive shaft 530. The bushing 572 is configured and dimensioned to come in contact with the ridge 568 such that as the drive shaft 530 is moved in the proximal direction the rotation link 564 is also withdrawn therewith. Concurrently or sequentially, the distal joint member 504 is returned into an aligned configuration. This is accomplished by retracting the distal segment 206 from the proximal joint member 502 by loosening the tension of the cables 205a, 205b, 205c, 205d, which then retracts the push rod 560 longitudinally in a proximal direction. The cam pins 582a, 584a are moved proximally in order to return the end effector 400 to the aligned configuration.

It will be understood that various modifications may be made to the embodiments disclosed herein. For example, the instrument 100 need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

The invention claimed is:

1. A surgical device, comprising:
    a jaw assembly comprising:
        a first jaw and a second jaw moveable relative to the first jaw; and
        a drive screw configured to move the second jaw relative to the first jaw;
    a pivoting linkage coupled to the proximal end of the jaw assembly, the pivoting linkage comprising a distal joint member and a proximal joint member, wherein the jaw assembly and the distal joint member define a first longitudinal axis extending between a proximal end of the jaw assembly and a distal end of the distal joint member, and the proximal joint member defines a second longitudinal axis; and
    a camming assembly coupled to the distal and proximal joint members, the camming assembly configured to pivot the jaw assembly relative to the proximal joint member about a pivot axis that is perpendicular to the first and second longitudinal axes from an aligned configuration in which the first and second longitudinal axes are substantially parallel to each other into a pivoted configuration in which the first and second longitudinal axes are substantially perpendicular to each other.

2. The surgical device of claim 1, further comprising:
    a drive shaft disposed within the pivoting linkage, the drive shaft configured to engage the drive screw and rotate in a first direction to move the second jaw relative to the first jaw when the jaw assembly is in one of the aligned configuration and the pivoted configuration.

3. The surgical device of claim 2, wherein in the aligned configuration the drive shaft is configured to engage the drive screw directly.

4. The surgical device of claim 3, wherein the pivoting linkage further comprises:
   a secondary gearing assembly comprising:
      a secondary first gear coupled to the primary first gear, the secondary first gear configured to rotate the jaw assembly about the first longitudinal axis when the jaw assembly and the distal joint member are in a pivoted configuration; and
      a secondary second gear coupled to the primary second gear, the secondary second gear configured to move the second jaw relative to the first jaw.

5. The surgical device of claim 4, wherein in the pivoted configuration the drive shaft is configured to engage the drive screw through the secondary second gear.

6. The surgical device of claim 2, wherein the pivoting linkage further comprises:
   a primary gearing assembly comprising:
      a primary first gear coupled to the jaw assembly configured to rotate the jaw assembly about the first longitudinal axis; and
      a primary second gear coupled to the drive screw configured to move the second jaw relative to the first jaw.

\* \* \* \* \*